US008636807B2

(12) United States Patent
Komistek

(10) Patent No.: US 8,636,807 B2
(45) Date of Patent: Jan. 28, 2014

(54) MOMENT INDUCED TOTAL ARTHROPLASTY PROSTHETIC

(75) Inventor: Richard D. Komistek, Knoxville, TN (US)

(73) Assignee: Depuy (Ireland), Co Cork (IE)

( * ) Notice: Subject to any disclaimer, the term of this patent is extended or adjusted under 35 U.S.C. 154(b) by 187 days.

(21) Appl. No.: 12/203,987

(22) Filed: Sep. 4, 2008

(65) Prior Publication Data
US 2009/0043396 A1 Feb. 12, 2009

Related U.S. Application Data

(63) Continuation of application No. PCT/US2006/010431, filed on Mar. 21, 2006.

(51) Int. Cl.
*A61F 2/38* (2006.01)
(52) U.S. Cl.
USPC .................. 623/20.33; 623/20.27; 623/20.29
(58) Field of Classification Search
None
See application file for complete search history.

(56) References Cited

U.S. PATENT DOCUMENTS

| 3,765,033 | A | 10/1973 | Goldberg |
| 3,869,731 | A | 3/1975 | Waugh |
| 4,209,861 | A | 7/1980 | Walker et al. |
| 4,215,439 | A | 8/1980 | Gold et al. |
| 4,262,368 | A | 4/1981 | Lacey |
| 4,340,978 | A | 7/1982 | Buechel et al. |
| 4,470,158 | A | 9/1984 | Pappas |
| 4,888,021 | A | 12/1989 | Forte et al. |
| 5,007,933 | A | 4/1991 | Sidebotham |
| 5,071,438 | A | 12/1991 | Jones et al. |
| 5,133,758 | A | 7/1992 | Hollister |
| 5,147,405 | A | 9/1992 | Van Zile |

(Continued)

FOREIGN PATENT DOCUMENTS

| DE | 19529824 A1 | 2/1997 |
| EP | 0636352 | 2/1995 |

(Continued)

OTHER PUBLICATIONS

European Search Report From Corresponding European Patent Application No. 06739287.8 Dated March 16, 2010, 3 Pages.

(Continued)

*Primary Examiner* — Thomas J Sweet
*Assistant Examiner* — Rebecca Preston

(57) ABSTRACT

Exemplary embodiments include a mobile bearing tibial tray insert including a medial condyle receiver spaced apart from a lateral condyle receiver, the mobile bearing tibial tray insert also including a stabilizing post, where the mobile bearing tibial tray insert is adapted to rotate around a substantially vertical rotational axis offset laterally from the stabilizing post. In addition, the foregoing embodiments may be supplemented by a tibial tray and femoral component to comprise a total knee replacement system. The disclosure also includes exemplary methods for imparting axial rotation to a prosthetic joint, the method comprising shifting the axis of axial rotation between a tibial prosthesis and a femoral prosthesis of a prosthetic knee joint by providing at least one of offsetting a stabilization post associated with a medial-lateral midline of a tibial insert of the tibial prosthesis, increasing the radii of a medial receiver of the tibial insert of the tibial prosthesis to a greater extent than the radii of a medial condyle of the femoral prosthesis, and increasing conformity between a medial receiver of the tibial insert of the tibial prosthesis and a medial condyle.

22 Claims, 9 Drawing Sheets

(56) References Cited

U.S. PATENT DOCUMENTS

| | | | |
|---|---|---|---|
| 5,219,362 A * | 6/1993 | Tuke et al. | 623/20.31 |
| 5,326,361 A | 7/1994 | Hollister | |
| 5,330,533 A | 7/1994 | Walker et al. | |
| 5,344,460 A | 9/1994 | Turanyi et al. | |
| 5,358,527 A | 10/1994 | Forte | |
| 5,370,699 A | 12/1994 | Hood | |
| 5,387,240 A | 2/1995 | Pottenger et al. | |
| 5,395,401 A | 3/1995 | Bahler | |
| 5,405,396 A | 4/1995 | Heldreth et al. | |
| 5,413,604 A * | 5/1995 | Hodge | 623/20.28 |
| 5,549,686 A | 8/1996 | Johnson et al. | |
| 5,571,194 A | 11/1996 | Gabriel | |
| 5,609,639 A | 3/1997 | Walker | |
| 5,609,643 A | 3/1997 | Colleran et al. | |
| 5,639,279 A * | 6/1997 | Burkinshaw et al. | 623/20.31 |
| 5,658,342 A | 8/1997 | Draganich et al. | |
| 5,681,354 A | 10/1997 | Eckhoff | |
| 5,683,468 A | 11/1997 | Pappas | |
| 5,702,458 A | 12/1997 | Burstein | |
| 5,702,466 A | 12/1997 | Pappas et al. | |
| 5,755,801 A | 5/1998 | Walker et al. | |
| 5,776,201 A | 7/1998 | Colleran et al. | |
| 5,778,537 A | 7/1998 | Leini | |
| 5,800,552 A | 9/1998 | Forte | |
| 5,811,543 A * | 9/1998 | Hao et al. | 540/123 |
| 5,824,100 A | 10/1998 | Kester | |
| 5,824,102 A | 10/1998 | Buscayret | |
| 5,871,543 A | 2/1999 | Hofmann | |
| 5,871,546 A | 2/1999 | Colleran et al. | |
| 5,935,173 A | 8/1999 | Roger | |
| 5,997,577 A | 12/1999 | Herrington | |
| 6,004,351 A | 12/1999 | Tomita | |
| 6,013,103 A | 1/2000 | Kaufman et al. | |
| 6,039,764 A * | 3/2000 | Pottenger et al. | 623/20.32 |
| 6,056,779 A | 5/2000 | Noyer et al. | |
| 6,080,195 A | 6/2000 | Colleran | |
| 6,123,729 A | 9/2000 | Insall | |
| 6,206,926 B1 | 3/2001 | Pappas | |
| 6,264,697 B1 | 7/2001 | Walker | |
| 6,299,646 B1 * | 10/2001 | Chambat et al. | 623/20.33 |
| 6,325,828 B1 | 12/2001 | Dennis et al. | |
| 6,344,059 B1 | 2/2002 | Krakovits | |
| 6,379,388 B1 | 4/2002 | Ensign et al. | |
| 6,443,991 B1 | 9/2002 | Running | |
| 6,475,241 B2 | 11/2002 | Pappas | |
| 6,491,726 B2 | 12/2002 | Pappas | |
| 6,540,787 B2 | 4/2003 | Biegun | |
| 6,558,426 B1 | 5/2003 | Masini | |
| 6,582,469 B1 | 6/2003 | Tornier | |
| 6,589,283 B1 | 7/2003 | Metzger et al. | |
| 6,730,128 B2 | 5/2004 | Burstein | |
| 6,764,516 B2 | 7/2004 | Pappas | |
| 6,770,099 B2 | 8/2004 | Andriacchi et al. | |
| 6,797,005 B2 | 9/2004 | Pappas | |
| 6,846,329 B2 | 1/2005 | McMinn | |
| 6,893,388 B2 | 5/2005 | Reising | |
| 6,893,467 B1 | 5/2005 | Bercovy | |
| 6,916,340 B2 | 7/2005 | Metzger et al. | |
| 6,926,738 B2 | 8/2005 | Wyss | |
| 6,972,039 B2 | 12/2005 | Metzger | |
| 6,986,791 B1 | 1/2006 | Metzger | |
| 7,025,788 B2 | 4/2006 | Metzger et al. | |
| 7,066,963 B2 * | 6/2006 | Naegerl | 623/20.32 |
| 7,081,137 B1 | 7/2006 | Servidio | |
| 7,105,027 B2 | 9/2006 | Lipman | |
| 7,160,330 B2 | 1/2007 | Axelson, Jr. | |
| 7,261,740 B2 | 8/2007 | Tuttle et al. | |
| 7,326,252 B2 | 2/2008 | Otto et al. | |
| 7,422,605 B2 * | 9/2008 | Burstein et al. | 623/20.33 |
| 7,572,292 B2 | 8/2009 | Crabtree et al. | |
| 7,658,767 B2 | 2/2010 | Wyss | |
| 7,678,152 B2 | 3/2010 | Suguro | |
| 7,842,093 B2 | 11/2010 | Peters | |
| 7,875,081 B2 | 1/2011 | Lipman | |
| 2003/0009232 A1 | 1/2003 | Metzger | |
| 2004/0243244 A1 | 12/2004 | Otto et al. | |
| 2004/0243245 A1 | 12/2004 | Plumet | |
| 2005/0096747 A1 | 5/2005 | Tuttle | |
| 2005/0143832 A1 | 6/2005 | Carson | |
| 2005/0154472 A1 | 7/2005 | Afriat | |
| 2005/0209701 A1 | 9/2005 | Suguro et al. | |
| 2005/0209702 A1 | 9/2005 | Todd et al. | |
| 2006/0015185 A1 | 1/2006 | Chambat et al. | |
| 2006/0178749 A1 | 8/2006 | Pendleton et al. | |
| 2007/0135926 A1 | 6/2007 | Walker | |
| 2008/0021566 A1 | 1/2008 | Peters | |
| 2008/0269596 A1 | 10/2008 | Revie | |
| 2009/0043396 A1 | 2/2009 | Komistek | |
| 2009/0306785 A1 | 12/2009 | Farrar | |
| 2009/0319047 A1 | 12/2009 | Walker | |
| 2009/0326663 A1 | 12/2009 | Dun | |
| 2010/0036500 A1 | 2/2010 | Heldreth et al. | |

FOREIGN PATENT DOCUMENTS

| | | |
|---|---|---|
| EP | 0732091 A2 | 9/1996 |
| EP | 1440675 A1 | 7/2004 |
| EP | 1591082 A2 | 11/2005 |
| EP | 1591082 A3 | 11/2005 |
| EP | 1591082 B1 | 9/2009 |
| EP | 1440675 B1 | 8/2010 |
| FR | 2417971 A1 | 9/1979 |
| FR | 2621243 A1 | 4/1989 |
| FR | 2787012 | 7/1998 |
| FR | 2787012 A1 | 6/2000 |
| FR | 2835178 | 1/2002 |
| JP | 8-500992 T | 2/1996 |
| JP | 2004167255 A | 6/2004 |
| WO | WO 02/09624 A1 | 2/2002 |
| WO | WO 2004058108 A1 | 7/2004 |
| WO | WO 2005/072657 | 1/2005 |
| WO | WO 2007/108804 | 9/2007 |
| WO | WO 2007108933 A1 | 9/2007 |
| WO | WO 2007119173 A2 | 10/2007 |
| WO | WO 2007119173 A3 | 12/2007 |

OTHER PUBLICATIONS

Australian Search Report for Corresponding Application No. 2006340364, Dec. 11, 2009, 2 Pages.

The Longitudinal Axis of the Knee and the Role of the Cruciate Ligaments in Controlling Transverse Rotation, James A. Shaw and David G. Murray, J.Bone Joint Surg Am. 1974;56:1603-1609.

PCT Notification Concerning Transmittal of International Preliminary Report for Corresponding International Application No. PCT/US2006/010431, Oct. 2, 2008, 6 Pages.

PCT Notification of Transmittal of International Search Report & Written Opinion for Corresponding International Application No. PCT/US2006/010431, Jun. 5, 2007, 8 Pages.

Barnes, C.L., et al, Kneeling Is Safe for Patients Implanted With Medial-Pivot Total Knee Arthroplasty Designs, Journal of Arthroplasty, vol. 00, No. 0 2010, 1-6, 6 Pages.

Blaha, et al., "Kinematics of the Human Knee Using an Open Chain Cadaver Model", Clinical Orthopaedics and Related Research, vol. 410 (2003); 25-34.

Dennis, et al, "A Multi-Center Analysis of Axial Femorotibial Rotation After Total Knee Arthroplasty", Clinical Orthopaedics 428 (2004): 180-89.

Fan, Cheng-Yu, et al, Primitive Results After Medial-Pivot Knee Arthroplasties: A Minimum 5-Year Follow-Up Study, The Journal of Arthroplasty, vol. 25, No. 3 2010, 492-496, 5 Pages.

Freeman, M.A.R., et al, The Movement of the Normal Tibio-Femoral Joint, The Journal of Biomechanics 38 (2005) (2), pp. 197-208, 12 Pgs.

Fuller, et al., "A Comparison of Lower-Extremity Skeletal Kinematics Measured Using Skin- and Pin-Mounted Markers", Human Movement Science 16 (1997) 219-242.

Hill, et al., "Tibiofemoral Movement 2: The Loaded and Unloaded Living Knee Studied by MRI", The Journal of Bone & Joint Surgery, vol. 82-B, No. 8 (Nov. 2000), 1196-1198.

(56) References Cited

OTHER PUBLICATIONS

Karachalios, et al., "A Mid-Term Clinical Outcome Study of the Advance Medial Pivot Knee Arthroplasty," www.sciencedirect.com, The Knee 16 (209); 484-488.

Komistek, et al., "In Vivo Fluoroscopic Analysis of the Normal Human Knee", Clinical Orthopaecis 410 (2003): 69-81.

Komistek, et al., "In Vivo Polyethylene Bearing Mobility Is Maintained in Posterior Stabilized Total Knee Arthroplasty", Clinical Orthopaedics 428 (2004): 207-213.

Koo, et al., "The Knee Joint Center of Rotation Is Predominantly on the Lateral Side During Normal Walking", Journal of Biomechanics, vol. 41 (2008): 1269-1273.

Mannan, et al., "The Medical Rotation Total Knee Replacement: A Clinical and Radiological Review at a Mean Follow-Up of Six Years", The Journal of Bone and Joint Surgery, vol. 91-B, No. 6 (Jun. 2009): 750-756.

Moonot, et al., "Correlation Between the Oxford Knee and American Knee Society Scores At Mid-Term Follow-Up", The Journal of Knee Surgery, vol. 22, No. 3 (Jul. 2009), 226-230.

Murphy, Michael Charles, *"Geometry and the Kinematics of the Normal Human Knee"*, Submitted to Massachusetts Institute of Technology (1990).

Nakagawa, et al., "Tibiofemoral Movement 3: Full Flexion in the Living Knee Studied by MRI", *The Journal of Bone and Joint Surgery*, vol. 82-B, No. 8 (Nov. 2000): 1199-1200.

Omori, et al., "The Effect of Geometry of the Tibial Polyethylene Insert on the Tibiofemoral Contact Kinematics in Advance Medial Pivot Total Knee Arthroplasty", *The Journal of Orthopaedic Science* (2009) 14:754-760.

Shakespeare, et al., "Flexion After Total Knee Replacement. A Comparison Between the Medial Pivot Knee and a Posterior Stabilised Knee," www.sciencedirect.com, *The Knee 13* (2006): 371-372.

Walker, et al., "Motion of a Mobile Bearing Knee Allowing Translation and Rotation", *Journal of Arthroplasty 17* (2002): 11-19.

Kurosawa, et al., "Geometry and Motion of the Knee for Implant and Orthotic Design", The Journal of Biomechanics 18 (1985), pp. 487-499, 12 Pages.

PCT Notification of Transmittal of the International Search Report and the Written Opinion of the International Searching Authority or the Declaration, Jun. 5, 2007, 89 Pages.

European Search Report From Corresponding EPO App. No. 12164381.1-2310, Dated May 18, 2012, 4 Pages.

European Search Report From Corresponding EPO App. No. 12181217.6-2310, Dated Jan. 15, 2013, 7 Pages.

Kessler, et al., "Sagittal Curvature of Total Knee Replacements Predicts In Vivo Kinematics," Clinical Biomechanics 22(1): 52-58, 2007.

Wang, et al., "Biomechanical Differences Exhibited During Sit-To-Stand Between Total Knee Arthroplasty Designs of Varying Radii," J Arthroplasty 21(8): 1196-1199, 2006.

Saari, et al., "The Effect of Tibial Insert Design on Rising From a Chair; Motion Analysis After Total Knee Replacement," Clin Biomech 19(9): 951-956, 2004.

Ranawat, "Design May Be Counterproductive for Optimizing Flexion After TKR," Olin Orthop Rel Res 416: 174-176, 2003.

D'Lima, et al., "Quadricepts Moment Arm and Quadriceps Forces After Total Knee Arthroplasty," Clin Orthop Rel Res 393:213-220, 2001.

Uvehammer, et al., "In Vivo Kinematics of Total Knee Arthroplasty: Flat Compared With Concave Tibial Joint Surface," J Orthop Res 18(6): 856-864, 2000.

Dennis, et al., "In Vivo Anteroposterior Femorotibial Translation of Total Knee Arthroplasty: A Multicenter Analysis," Clin Orthop Rel Rex, 356: 47-57, 1998.

Clary, et al., "Kinematics of Posterior Stabilized and Cruciate Retaining Knee Implants During an In Vitro Deep Knee Bend," 54th Annual Meeting of the Orthopaedic Research Society, Poster No. 1983, Mar. 2008.

Wang, et al., "A Biomechanical Comparison Between the Single-Axis and Multi-Axis Total Knee Arthroplasty Systems for Stand-To-Sit Movement," Clin Biomech 20(4): 428-433, 2005.

Dennis, et al., "Multicenter Determination of In Vivo Kinematics After Total Knee Arthroplasty," Clin. Orthop. Rel. Res., 416, 37-57, 21 Pages, 2003.

Yoshiya et al., "In Vivo Kinematic Comparison of Posterior Cruciate Retaining and Posterior Stabilized Total Knee Arthroplasties Under Passive and Weight-Bearing Conditions," J. Arthroplasty, vol. 20, No. 6, 2005, 7 Pages.

Bertin et al., "In Vivo Determination of Posterior Femoral Rollback for Subjects Having a Nexgen Posterior Cruciate-Retaining Total Knee Arthroplasty," J. Arthroplasty, vol. 17, No. 8, 2002, 9 Pages.

Suggs, et al., "Three Dimensional Tibiofemoral Articular Contact Kinematics of a Cruciate-Retaining Total Knee Arthroplasty," JBJS-AM, vol. 88, No. 2, 2006, 10 Pages.

Dennis, et al., "In Vivo Determination of Normal and Anterior Cruciate Ligament-Deficient Knee Kinematics," J. Biomechanics, 38, 241-253, 2005, 13 Pages.

Li et al., "Anterior Cruciate Ligament Deficiency Alters the In Vivo Motion of the Tibiofemoral Cartilage Contact Points in Both Anteroposterior and Mediolateral Directions," JBJS-AM, vol. 88, No. 8, Aug. 2006, 10 Pages.

Ries, "Effect of ACL Sacrifice, Retention, or Substitution on K After TKA," http/www.orthosupersite, com/view.asp?rid=23134, Aug. 2007, 5 Pages.

Ferris, "Matching Observed Spiral Form Curves to Equations of Spirals in 2-D Images," The First Japanese-Australian Joint Seminar, 7 Pages.

Goodfellow et al., "The Mechanics of the Knee and Prosthesis Design," The Journal of Bone and Joint Surgery, vol. 60-B, No. 3, 12 Pages, Aug. 1978.

"Vanguard Complete Knee System," Biomet, Available At http://www.biomet.com/patients/vanguard_complete.cfm, Downloaded on Feb. 2009, 3 Pages.

"Nexgen Complete Knee Solution Cruciate Retaining Knee (CR)," Zimmer, Available At http://zimmer.com.au/ctl?template=pc&op=global&action=&template=pc&id-356, Downloaded on Feb. 18, 2009, 1 Page.

Scorpio Knee TS Single Axis Revision Knee System, Stryker Orthopaedics, http://www.stryker.com/stellent/groups/public/documents/web_prod/023609.pdf, 6 Pages, Literature No. LSKTS/B, 2004.

P. Johal et al., "Tibio-Femoral Movement in the Living Knee. A Study of Weight Bearing and Non-Weight Bearing Knee Kinematics Using 'Interventional' MRI," Journal of Biomechanics, vol. 38, Issue 2, Feb. 2005, pp. 269-276, 8 Pages.

Andriacchi, T.P., "The Effect of Knee Kinematics, Gait and Wear on the Short and Long-Term Outcomes of Primary Knee Replacement," NIH Consensus Development Conference on Total Knee Replacement, pp. 61-62, Dec. 8-10, 2003, 4 Pages.

Asano et al., "In Vivo Three-Dimensional Knee Kinematics Using a Biplanar Image-Matching Technique," Clin Orthop Rel Res, 388:157-166, 2001, 10 Pages.

EPO Search Report From Corresponding EPO Patent Application No. 12164381.1-1654, Dated Mar. 7, 2013, 3 Pages.

Japanese Search Report for Corresponding Patent Application No. 2009-501393, Dated Oct. 26, 2010, 5 Pages.

European Search Report in EPO App. No. 10162138.1 Dated Aug. 30, 2010, 7 Pages.

European Search Report in EPO App. No. 09164478.1-2310 Dated Oct. 20, 2009, 6 Pages.

European Search Report in EPO App. No. 09164478.1-2310 Dated Apr. 28, 2010, 12 Pages.

\* cited by examiner

MOMENT INDUCED TOTAL ARTHROPLASTY PROSTHETIC

CROSS REFERENCE TO RELATED APPLICATIONS

This application is a continuation that claims priority under 35 U.S.C. §120 to Patent Cooperation Treaty Application Serial No. PCT/US2006/010431 filed on Mar. 21, 2006, entitled "MOMENT INDUCED TOTAL ARTHROPLASTY PROSTHETIC," the disclosure and amended disclosure of which are hereby incorporated by reference.

RELATED ART

1. Field of the Invention

The exemplary embodiments disclosed herein are directed to implanted prosthetic devices and, more specifically, to implanted prosthetic joints that simulate the natural biomechanics of native mammalian joints. Further exemplary embodiments also encompass methods of inducing moments within an implanted prosthetic joint, as well as implanted prosthetic devices that incorporate induced moments.

2. Brief Discussion of Related Art

Previous research studies have documented that the amount of rotation occurring in the knee, during walking and high flexion activities, varies greatly between a natural knee (no prior surgeries and no history of clinical abnormalities) and a surgically revised knee such as those having undergone total knee arthroplasty (TKA). The axial femorotibial rotational pattern of the femur relative to the tibia during flexion of a natural knee induces tibia internal rotation relative to the femur, and tibia external rotation relative to the femur as the knee extends. This internal rotational mechanism results in part from the length and tension within the cruciate and collateral ligaments and anatomic variances in dimensions of the medial and lateral femoral and tibial condyles.

The exact axial femorotibial rotational pattern after TKA is less clear, but has been shown to vary considerably. Many have hypothesized that decreases in axial rotation after TKA may be related to removal or alteration of the cruciate ligaments and/or failure to exactly duplicate geometry of the medial and lateral femoral and tibial condyles, although most hypothesize that this reduced motion derives from the inability to reproduce correct condylar geometries.

A multicenter, in vivo, weight-bearing kinematic analysis has demonstrated similar average axial rotational values in fixed versus mobile bearing TKA prosthetics. Controversy exists, however, as to the exact site of axial rotation (superior vs. inferior aspect of the tibial insert) in mobile bearing TKA prosthetics. Many fixed and mobile bearing TKA prosthetics have demonstrated significantly reduced axial rotation, while others have documented that TKA patients often experience a reverse rotation pattern, where the tibia externally rotates about the femur with increasing knee flexion.

INTRODUCTION TO THE INVENTION

The exemplary embodiments disclosed herein are directed to implantable prosthetic devices simulating the natural biomechanics of native mammalian joints. These exemplary embodiments induce moments within an implantable prosthetic joint to impart rotational movement between joint components. The exemplary embodiments also encompass the joint components themselves that induce moments, as well as methods for inducing moments to impart rotation between complimentary prosthetic components within an implantable joint.

It is a first aspect to provide a prosthetic tibial insert including medial and lateral receivers for receiving a pair of condyles of a femoral prosthesis, the prosthetic tibial tray insert also including a stabilizing post, where the centerline of the stabilizing post is offset from at least one of an anterior-posterior centerline of the prosthetic tibial tray insert and a medial-lateral centerline of the prosthetic tibial tray insert.

In a more detailed embodiment of the first aspect, the prosthetic tibial tray rotates with respect to the prosthetic tibial tray implant about a first axis of rotation, and the first axis of rotation is offset laterally with respect to the stabilizing post. In yet another more detailed embodiment, a posterior aspect of the stabilizing post is not rounded. In a further detailed embodiment, the stabilizing post is onset anteriorly from an anterior-posterior centerline of the prosthetic tibial tray insert. In still a further detailed embodiment, the stabilizing post is offset posteriorly from an anterior-posterior centerline of the prosthetic tibial tray insert. In a more detailed embodiment, the prosthetic tibial tray insert includes a recess adapted to receive a projection from the prosthetic tibial tray implant about which the prosthetic tibial tray insert rotates with respect to the prosthetic tibial tray implant. In a more detailed embodiment, the prosthetic tibial tray insert includes a projection adapted to be received by a recess of the prosthetic tibial tray implant about which the prosthetic tibial tray insert rotates with respect to the prosthetic tibial tray implant. In another more detailed embodiment, the prosthetic tibial tray rotates with respect to the prosthetic tibial tray implant about a first axis of rotation, the prosthetic tibial tray insert rotates with respect to the femoral prosthesis about a second axis of rotation, and the first axis of rotation is not coaxial with the second axis of rotation. In yet another more detailed embodiment, the stabilizing post is offset medially between about 0.1 millimeters to about 30 millimeters with respect to the first axis of rotation.

It is a second aspect to provide a prosthetic tibial insert comprising a prosthetic tibial tray insert including medial and lateral spaced apart receivers for receiving a pair of condyles of a femoral prosthesis, the prosthetic tibial tray insert also including a stabilizing post, where the prosthetic tibial tray insert is adapted to rotate, with respect to a prosthetic tibial tray implant secured a patient's tibia, around a rotational axis generally perpendicular to the prosthetic tibial tray insert, where the rotational axis is offset laterally from the stabilizing post.

In a more detailed embodiment of the second aspect, the stabilizing post is offset medially with respect to the rotational axis. In yet another more detailed embodiment, the rotational axis is offset anteriorly from an anterior-posterior centerline of the prosthetic tibial tray insert. In still a further detailed embodiment, the rotational axis is offset posteriorly from an anterior-posterior centerline of the prosthetic tibial tray insert. In a more detailed embodiment, the prosthetic tibial tray insert includes a recess adapted to receive a projection from the prosthetic tibial tray implant about which the prosthetic tibial tray insert rotates with respect to the prosthetic tibial tray implant. In a more detailed embodiment, the prosthetic tibial tray insert includes a projection adapted to be received by a recess of the prosthetic tibial tray implant about which the prosthetic tibial tray insert rotates with respect to the prosthetic tibial tray implant. In another more detailed embodiment, the prosthetic tibial tray insert rotates with respect to the prosthetic tibial tray implant about a first axis of rotation, the prosthetic tibial tray insert rotates with respect to the femoral prosthesis about a second axis of rotation, and the first axis of rotation is not coaxial with the second axis of rotation. In yet another more detailed embodiment, the stabilizing post is offset medially from a medial-lateral centerline of the prosthetic tibial tray insert between about 0.1 millimeters to about 20 millimeters.

It is a third aspect to provide a prosthetic tibial tray insert including lateral and medial condyle receivers for receiving lateral and medial condyles of a femoral prosthesis, the medial condyle receiver has substantially greater conformity to the medial femoral condyle than does the lateral condyle receiver with respect to the lateral femoral condyle, the combination of lesser conformity laterally and substantially greater conformity medially creating rotation about a substantially vertical axis between the prosthetic tibial tray insert and the condyles of the femoral prosthesis.

In a more detailed embodiment of the third aspect, the prosthetic tibial tray insert includes a recess adapted to receive a projection from a prosthetic tibial tray implant so the prosthetic tibial tray insert rotates with respect to the prosthetic tibial tray implant about a first rotational axis, and the first rotational axis is offset laterally from a medial-lateral centerline of the prosthetic tibial tray insert. In yet another more detailed embodiment, the prosthetic tibial tray insert includes a projection adapted to be received by a recess of a prosthetic tibial tray implant so the prosthetic tibial tray insert rotates with respect to the prosthetic tibial tray implant about a first rotational axis, and the first rotational axis is offset laterally from a medial-lateral centerline of the prosthetic tibial tray insert. In a further detailed embodiment, the prosthetic tibial tray insert rotates with respect to the prosthetic tibial tray implant about the first rotational axis, the prosthetic tibial tray insert rotates with respect to the femoral prosthesis about the substantially vertical axis, and the first rotational axis is not coaxial with the substantially vertical axis. In still a further detailed embodiment, the substantially vertical axis is offset laterally from a medial-lateral centerline of the prosthetic tibial tray insert. In a more detailed embodiment, the lateral condyle receiver includes at least one of a convex shape or a sequentially sloped from anterior to posterior shape, and the medial condyle receiver includes a concave shape for receiving a convex medial condyle of the femoral prosthesis.

It is a fourth aspect to provide an implantable prosthetic knee joint comprising: (a) a femoral prosthetic; and (b) a tibial tray prosthetic including a prosthetic tibial tray insert rotationally repositionable with respect to the tibial tray about a first rotational axis, the tibial tray insert including medial and lateral spaced apart receivers for receiving a pair of condyles of the femoral prosthetic,—where the first rotational axis is offset laterally from a medial-lateral centerline of the prosthetic tibial tray insert.

In a more detailed embodiment of the fourth aspect, the first rotational axis is offset laterally between about 0.1 millimeters to about 30 millimeters from the medial-lateral centerline of the prosthetic tibial tray insert. In yet another more detailed embodiment, a stabilizing post that is offset medially from a medial-lateral centerline of the prosthetic tibial tray insert, where the first rotational axis is offset laterally between about 0.1 millimeters to about 30 millimeters from the stabilizing post. In a further detailed embodiment, the stabilizing post is offset from an anterior-posterior centerline of the prosthetic tibial tray insert. In still a further detailed embodiment, the femoral prosthetic includes lateral and medial condyles, the prosthetic tibial tray insert includes lateral and medial condyle receivers for receiving the lateral and medial condyles of a femoral prosthesis, and the medial condyle receiver has substantially greater conformity to the medial femoral condyle than does the lateral condyle receiver with respect to the lateral femoral condyle, and wherein up to 12.5 mm of translation to occurs for the medial condyle with respect to the medial receiver from 20 degrees of knee flexion to maximum knee flexion. In a further detailed embodiment, the medial condyle is larger than the lateral condyle. In yet another further detailed embodiment, a posterior aspect of the stabilizing post offset is either rounded or not rounded.

It is a fifth aspect to provide an implantable prosthetic knee joint comprising: (a) a femoral prosthetic; and (b) a tibial tray prosthetic including a prosthetic tibial tray insert, the tibial tray insert including medial and lateral spaced apart condyle receivers for receiving a pair of condyles of the femoral prosthetic, where the medial condyle receiver has substantially greater conformity to the medial femoral condyle than does the lateral condyle receiver with respect to the lateral femoral condyle, the combination of lesser conformity laterally and substantially greater conformity medially creating rotation about a substantially vertical axis between the prosthetic tibial tray insert and the condyles of the femoral prosthetic, and wherein up to 12.5 mm of translation to occurs for the medial condyle with respect to the medial receiver from 20 degrees of knee flexion to maximum knee flexion.

In a more detailed embodiment of the fifth aspect, the knee joint further includes a stabilizing post that is offset laterally from a medial-lateral centerline of the prosthetic tibial tray insert, and the stabilizing post is offset medially between about 0.1 millimeters to about 20 millimeters from a medial-lateral centerline of the prosthetic tibial tray insert. In yet another more detailed embodiment, the lateral condyle receiver includes at least one of a convex shape or a dual-sloped from anterior to posterior shape, and the medial condyle receiver includes a concave shape for receiving a convex medial condyle of the femoral prosthetic. In a further detailed embodiment, the femoral prosthetic includes a cam to ride upon the stabilizing post, where the cam is shifted to match the shift of the stabilizing post, and a posterior aspect of the stabilizing post to be contacted by the cam is rounded.

It is a sixth aspect to provide an implantable prosthetic knee joint comprising: (a) a femoral prosthesis adapted to be mounted to a patient's natural femur; (b) a tibial tray prosthesis adapted to be mounted to the patients' natural tibia; and (c) a prosthetic tibial tray insert including medial and lateral spaced apart receivers for receiving medial and lateral condyles of the femoral prosthesis, the medial condyle receiver has substantially greater conformity to the medial femoral condyle than does the lateral condyle receiver with respect to the lateral femoral condyle, the combination of lesser conformity laterally and substantially greater conformity medially creating rotation about a substantially vertical axis between the prosthetic tibial tray insert and the condyles of the femoral prosthesis, and wherein up to 12.5 mm of translation to occurs for the medial condyle with respect to the medial receiver from 20 degrees of knee flexion to maximum knee flexion.

In a more detailed embodiment of the sixth aspect, the prosthetic tibial tray insert is adapted to rotate, with respect to the tibial tray prosthesis, around a rotational axis perpendicular to the prosthetic tibial tray insert, where the rotational axis is laterally offset from a medial-lateral centerline of the prosthetic tibial tray insert. In yet another more detailed embodiment, the lateral condyle receiver includes at least one of a convex shape or a dual-sloped from anterior to posterior shape, and the medial condyle receiver includes a concave shape, allowing for 12.5 mm of translational laxity from 20 degrees of flexion to maximum knee flexion, for receiving a convex medial condyle of the femoral prosthetic. In a further detailed embodiment, the rotational axis is offset from an anterior-posterior centerline of the prosthetic tibial tray insert. In still a further detailed embodiment, the rotational axis is not coaxial with the substantially vertical axis. In a more detailed embodiment, the prosthetic tibial tray insert includes a recess adapted to receive a projection from the tibial tray prosthesis about which the prosthetic tibial tray insert rotates with respect to the tibial tray prosthesis. In a further detailed embodiment, the prosthetic tibial tray insert includes a projection adapted to be received by a recess of the tibial tray prosthesis about which the prosthetic tibial tray insert rotates with respect to the tibial tray prosthesis. In still a further detailed embodiment, the tibial tray prosthesis and the prosthetic tibial tray insert form a fixed bearing prosthetic, and the prosthetic tibial tray insert includes a stabilizing post offset laterally from a medial-lateral centerline of the prosthetic tibial tray insert. In a more detailed embodiment, the prosthetic tibial tray insert includes a stabilizing post offset medially from a medial-lateral centerline of the prosthetic tibial tray insert.

It is a seventh aspect to provide an implantable prosthetic knee joint comprising: (a) a femoral component for mounting to a natural femur; and (b) a tibial component for mounting to a natural tibia, the tibial component including lateral and medial condyle receivers for receiving lateral and medial condyles of the femoral component, the lateral condyle receiver having at least one of a convex shape or a dual-sloped from anterior to posterior shape, the medial condyle receiver has substantially greater conformity to the medial femoral condyle than does the lateral condyle receiver with respect to the lateral femoral condyle, the combination of lesser conformity laterally and substantially greater conformity medially, allowing up to 12.5 mm of translational laxity, creating a moment around an axis of rotation to impart horizontal rotation between the tibial component and the condyles of the femoral component.

In a more detailed embodiment of the seventh aspect, the tibial component includes a tibial tray that is to be mounted to a natural tibia, and the tibial tray insert includes a recess to receive a projection from the tibial tray of the tibial component about which the tibial tray insert rotates with respect to the tibial tray. In yet another more detailed embodiment, the tibial component includes a tibial tray that is to be mounted to a natural tibia, and the tibial tray insert includes a projection to be received by a recess of the tibial tray of the tibial component about which the tibial tray insert rotates with respect to the tibial tray. In a further detailed embodiment, the tibial tray insert rotates with respect to the tibial tray about a second rotational axis, the tibial tray insert rotates with respect to the femoral component along the axis of rotation, and the axis of rotation is eccentric to the second rotational axis. In still a further detailed embodiment, the axis of rotation is offset laterally from a medial-lateral centerline of the tibial tray insert, the lateral condyle receiver includes at least one of a convex shape or a dual-sloped from anterior to posterior shape, and the medial condyle receiver includes a concave shape for receiving a convex medial condyle of the femoral prosthesis. In a more detailed embodiment, the prosthetic tibial tray insert includes a stabilizing post offset medially from a medial-lateral centerline of the prosthetic tibial tray insert.

It is an eighth aspect to provide a mobile bearing prosthetic knee joint comprising: (a) a tibial prosthesis for implantation into the tibia of a recipient, the tibial prosthesis including a tibial tray and a tibial insert, mounted to the tibial tray, that is rotationally repositionable with respect to the tibial tray to induce a moment about a point of rotation of the tibial tray that is offset laterally from a medial-lateral centerline of the tibial tray, the tibial tray including a medial receiver and a tibial receiver; and (b) a femoral component for implantation into the femur of the recipient, the femoral component including a medial condyle that is received within the medial receiver of the tibial tray, and a lateral condyle that is received within the lateral receiver of the tibial tray.

In a more detailed embodiment of the eighth aspect, the tibial tray includes a stabilizing post medially offset from the point of rotation of the tibial tray. In yet another more detailed embodiment, the medial receiver has substantially greater conformity to the medial condyle than does the lateral receiver with respect to the lateral condyle, the combination of lesser conformity laterally and substantially greater conformity medially creating another moment around an axis of rotation to impart horizontal rotation between the tibial tray and the receivers of the femoral component. In a further detailed embodiment, the stabilizing post is medially offset between about 0.1 millimeters to about 30 millimeters from the point of rotation of the tibial tray. In still a further detailed embodiment, the lateral receiver includes at least one of a convex shape or a sloped from anterior to posterior shape, and the medial receiver includes a concave shape for receiving a convex medial condyle of the femoral prosthesis.

It is a ninth aspect to provide a fixed bearing prosthetic knee joint comprising: (a) a tibial prosthesis to be mounted to a tibia of a recipient, the tibial prosthesis including a medial receiver and a lateral receiver; and (b) a femoral prosthesis to be mounted to a femur of the recipient, the femoral prosthesis including a medial condyle that is to be received by the medial receiver, and a lateral condyle that is to be received by the lateral receiver, where the medial receiver has substantially greater conformity to the medial condyle than does the lateral receiver with respect to the lateral condyle, the combination of lesser conformity laterally and substantially greater conformity medially generating a moment about which the tibial prosthesis rotates with respect to the femoral prosthesis.

In a more detailed embodiment of the ninth aspect, the tibial prosthesis includes a tibial tray and a tibial insert mounted to the tibial tray, the tibial insert including the medial receiver and the lateral receiver. In yet another more detailed embodiment, the lateral receiver includes at least one of a convex shape or a dual-sloped from anterior to posterior shape, and the medial receiver includes a concave shape for receiving a convex medial condyle of the femoral prosthesis. In a further detailed embodiment, at least one of the tibial insert and tibial tray includes a stabilizing post adapted to be contacted by the femoral prosthesis. In yet a further more detailed embodiment, the stabilizing post is laterally offset between about 0.1 millimeters to about 20 millimeters from a medial-lateral centerline of the tibial insert. In another more detailed embodiment, the posterior aspect of the stabilizing post is rounded to have a concave or convex shape. In still another more detailed embodiment, the femoral prosthesis includes a cam adapted to rotationally ride on the posterior aspect of the stabilizing post, where a topography of the cam is arcuately convex or concave to receive the rounded posterior aspect of the stabilizing post.

It is a tenth aspect to provide a method of imparting axial rotation to an implantable prosthetic joint, the method comprising generating a moment about an axis of rotation between a femoral component and a tibial component of a prosthetic joint to impart axial rotation between the two components, the act of generating the moment includes substantially increasing conformity between a medial receiver of the tibial component and a medial condyle of the femoral component and substantially decreasing conformity between a lateral receiver of the tibial component and a lateral condyle of the femoral component.

It is an eleventh aspect to provide a method of imparting axial rotation to an implantable fixed bearing prosthetic knee joint, the method comprising shifting an axis of axial rotation between a tibial prosthesis and a femoral prosthesis of a fixed bearing prosthetic knee joint by providing at least one of: (a) offsetting a stabilization post laterally from a medial-lateral midline of a tibial insert of the tibial prosthesis, the tibial insert providing a bearing surface upon which the femoral prosthesis rides, and (b) substantially increasing conformity between a medial receiver of the tibial insert of the tibial prosthesis and a medial condyle of the femoral prosthesis in relation to conformity between a lateral receiver of the tibial insert of the tibial prosthesis and a lateral condyle of the femoral prosthesis.

In a more detailed embodiment of the eleventh aspect, the method includes shifting the axis of axial rotation between the tibial prosthesis and the a femoral prosthesis of the a fixed bearing prosthetic knee joint includes offsetting the stabilization post laterally from the medial-lateral midline of the tibial insert of the tibial prosthesis. In yet another more detailed embodiment, the method includes shifting the axis of axial rotation between the tibial prosthesis and the femoral prosthesis of the fixed bearing prosthetic knee joint includes substantially increasing conformity between the medial receiver of the tibial insert and the medial condyle of the femoral prosthesis. In a further detailed embodiment, the lateral receiver includes at least one of a convex shape or a dual-sloped from anterior to posterior shape, and the medial receiver includes a concave shape for receiving a convex medial condyle of the femoral prosthesis.

It is a twelfth aspect to provide a method of imparting axial rotation to an implantable prosthetic joint, the method comprising generating a moment about, an axis of rotation, between a femoral component and a tibial component of a fixed bearing prosthetic joint to impart axial rotation between the two components, the act of generating the moment includes laterally offsetting a stabilizing post associated with at least one of the femoral component and the tibial component from a medial-lateral midline associated with the component that includes the stabilizing post.

It is a thirteenth aspect to provide a method of imparting axial rotation to an implantable mobile bearing prosthetic knee joint, the method comprising at least one of the following acts: (a) shifting an axis of axial rotation between a tibial prosthesis and a femoral prosthesis of a mobile bearing prosthetic knee joint by offsetting a stabilization post medially from a medial-lateral midline of a tibial insert of the tibial prosthesis; (b) shifting an axis of axial rotation between a tibial tray and a tibial tray insert of a mobile bearing prosthetic knee joint by offsetting a point of rotation between the tibial tray and tibial tray insert laterally from a medial-lateral midline of the tibial tray insert; and (c) shifting an axis of axial rotation between a tibial prosthesis and a femoral prosthesis of a mobile bearing prosthetic knee joint by substantially increasing conformity between a medial receiver of the tibial insert of the tibial prosthesis and a medial condyle of the femoral prosthesis in relation to conformity between a lateral receiver of the tibial insert of the tibial prosthesis and a lateral condyle of the femoral prosthesis.

It is a fourteenth aspect to provide a method of imparting axial rotation to an implantable prosthetic joint, the method comprising generating a moment about an axis of rotation between an anteriorly positioned stabilizing post of a tibial prosthesis and a cam of a femoral prosthesis to impart axial rotation between the two prostheses, the act of generating the moment includes at least one of rounding the posterior aspect of the stabilizing post of the tibial prosthesis and concaving the cam of the femoral prosthesis.

It is a fifteenth aspect to provide an implantable prosthetic knee joint comprising: (a) a femoral prosthetic having a pair of condyles interposed by a cam; and (b) a tibial tray prosthetic including a prosthetic tibial tray insert including medial and lateral spaced apart receivers for receiving the pair of condyles of the femoral prosthetic, the prosthetic tibial tray insert also including a stabilizing post having a rounded posterior aspect interfacing with the cam of the femoral prosthetic to at least partially guide axial rotation of the femoral prosthetic with respect to the tibial tray.

It is a sixteenth aspect to provide an implantable prosthetic knee joint comprising: (a) a femoral prosthetic having a pair of condyles interposed by an arcuately concave or convex cam; and (b) a tibial tray prosthetic including a prosthetic tibial tray insert including medial and lateral spaced apart receivers for receiving the pair of condyles of the femoral prosthetic, the prosthetic tibial tray insert also including a stabilizing post having a rounded posterior aspect adapted to interface with the arcuately concave or convex cam of the femoral prosthetic.

It is a seventeenth aspect to provide a prosthetic tibial tray insert comprising a prosthetic tibial tray insert including medial and lateral spaced apart receivers for receiving a pair of condyles of a femoral prosthesis, the prosthetic tibial tray insert also including a stabilizing post with a rounded, convex posterior aspect adapted to facilitate rotation of the formal prosthesis about a rotational axis, where the stabilizing post is medially offset from a media-lateral centerline of the prosthetic tibial tray insert.

It is an eighteenth aspect to provide a method of imparting axial rotation to an implantable prosthetic joint, the method comprising generating a moment about an axis of rotation between a tibial prosthetic tray and a tibial prosthetic insert, the act of generating the moment includes laterally offsetting, from a medial-lateral centerline of the tibial prosthetic insert, a point of rotation between the tibial prosthetic tray and the tibial prosthetic insert, where the offset is between about 0.1 millimeters to about 20 millimeters.

It is a nineteenth aspect to provide a mobile bearing posterior stabilized knee joint comprising: (a) a femoral prosthetic component including a medial condyle and a lateral condyle; and (b) a tibial prosthetic component comprising a tibial tray insert rotationally repositionable about a first rotational axis with respect to a tibial tray, the first rotational axis being laterally offset from a medial-lateral centerline of the tibial tray, the tibial tray also including a post medially offset from the rotational axis of the tibial tray so that the post is medial with respect to the first rotational axis, the tibial tray further including a medial receiver to receive the medial condyle and a lateral receiver to receive the lateral condyle, wherein a posterior aspect of the post is not rounded, wherein conformity between the medial condyle and the condyle receiver is substantially greater than conformity between lateral condyle and the lateral condyle receiver, wherein the lateral condyle receiver is sloped from anterior to posterior, and wherein the femoral prosthetic component interfaces with the tibial prosthetic component to comprise a joint.

It is a twentieth aspect to provide a mobile bearing posterior stabilized knee joint comprising: (a) a femoral prosthetic component including a medial condyle and a lateral condyle; and, (b) a tibial prosthetic component comprising a tibial tray insert rotationally repositionable about a first rotational axis with respect to a tibial tray, the first rotational axis being laterally offset from a medial-lateral centerline of the tibial tray, the tibial tray also including a post medially offset from the first rotational axis of the tibial tray so that the post is medial with respect to the first rotational axis, the tibial tray further including a medial receiver to receive the medial condyle and a lateral receiver to receive the lateral condyle, wherein a posterior aspect of the post is not rounded, wherein conformity between the medial condyle and the condyle receiver is substantially greater than conformity between lateral condyle and the lateral condyle receiver, wherein the lateral condyle receiver is sloped from anterior to posterior, and wherein the femoral prosthetic component interfaces with the tibial prosthetic component to comprise a joint.

It is a twenty-first aspect to provide a fixed bearing posterior stabilized knee joint comprising: (a) a femoral prosthetic component including a medial condyle and a lateral condyle; and, (b) a tibial prosthetic component including a post laterally offset from the medial-lateral centerline of the tibial prosthetic component, the tibial prosthetic component further including a medial receiver to receive the medial condyle and a lateral receiver to receive the lateral condyle, wherein a posterior aspect of the post is rounded, wherein conformity between the medial condyle and the condyle receiver is substantially greater than conformity between lateral condyle and the lateral condyle receiver, wherein the lateral condyle receiver is sloped from anterior to posterior, and wherein the femoral prosthetic component interfaces with the tibial prosthetic component to comprise a joint.

It is a twenty-second aspect to provide a mobile bearing posterior cruciate retaining knee joint comprising: (a) a femoral prosthetic component including a medial condyle and a lateral condyle; and (b) a tibial prosthetic component comprising a tibial tray insert rotationally repositionable about a first rotational axis with respect to a tibial tray, the first rotational axis being laterally offset from a medial-lateral centerline of the tibial tray, the tibial tray further including a medial receiver to receive the medial condyle and a lateral receiver to receive the lateral condyle, wherein conformity between the medial condyle and the condyle receiver is substantially greater than conformity between lateral condyle and the lateral condyle receiver, wherein the substantially greater conformity includes translational laxity between the medial condyle and the medical receiver of up to about 12.5 mm of translational laxity at greater than 20 degrees of knee flexion, wherein the lateral condyle receiver is sloped from anterior to posterior, and wherein the femoral prosthetic component interfaces with the tibial prosthetic component to comprise a joint.

It is a twenty-third aspect to provide a fixed bearing posterior cruciate retaining knee joint comprising: (a) a femoral prosthetic component including a medial condyle and a lateral condyle; and, (b) a tibial prosthetic component including a medial receiver to receive the medial condyle and a lateral receiver to receive the lateral condyle, wherein conformity between the medial condyle and the condyle receiver is substantially greater than conformity between lateral condyle and the lateral condyle receiver, wherein the substantially greater conformity includes translational laxity between the medial condyle and the medical receiver of up to about 12.5 mm of translational laxity at greater than 20 degrees of knee flexion, wherein the lateral condyle receiver is sloped from anterior to posterior, wherein the medial condyle is substantially larger than the lateral condyle, and wherein the femoral prosthetic component interfaces with the tibial prosthetic component to comprise a joint.

It is a twenty-fourth aspect to provide a mobile bearing posterior cruciate retaining knee joint comprising: (a) a femoral prosthetic component including a medial condyle and a lateral condyle; and, (b) a tibia prosthetic component comprising a tibial tray insert rotationally repositionable about a first rotational axis with respect to a tibial tray, the first rotational axis being laterally offset from a medial-lateral centerline of the tibial tray, the tibial tray further including a medial receiver to receive the medial condyle and a lateral receiver to receive the lateral condyle, wherein conformity between the medial condyle and the condyle receiver is substantially greater than conformity between lateral condyle and the lateral condyle receiver, wherein the lateral condyle receiver is sloped from anterior to posterior, wherein the medial condyle is substantially larger than the lateral condyle, and wherein the femoral prosthetic component interfaces with the tibial prosthetic component to comprise a joint.

It is a twenty-fifth aspect to provide a prosthetic tibial insert comprising: (a) a prosthetic tibial tray insert including medial and lateral receivers for receiving a pair of condyles of a femoral prosthesis, the prosthetic tibial tray insert also including a stabilizing post; and (b) a prosthetic tibial tray implant operatively coupled to the tibial tray, where the prosthetic tibial tray insert rotates with respect to the prosthetic tibial tray implant, where the prosthetic tibial tray rotates with respect to the prosthetic tibial tray implant about a first axis of rotation, and the first axis of rotation is offset laterally with respect to the stabilizing post.

In a more detailed embodiment of the twenty-fifth aspect, a posterior aspect of the stabilizing post is not rounded. In yet another more detailed embodiment, the stabilizing post is offset at least one of anteriorly and posteriorly from an anterior-posterior centerline of the prosthetic tibial tray insert. In a further detailed embodiment, the prosthetic tibial tray insert includes a recess adapted to receive a projection from the prosthetic tibial tray implant so the prosthetic tibial tray insert rotates, about the first axis of rotation, with respect to the prosthetic tibial tray implant. In still a further detailed embodiment, the prosthetic tibial tray insert includes a projection adapted to be received by a recess of the prosthetic tibial tray implant so the prosthetic tibial tray insert rotates, about the first axis of rotation, with respect to the prosthetic tibial tray implant. In a more detailed embodiment, the prosthetic tibial tray insert rotates with respect to the femoral prosthesis about a second axis of rotation, and the first axis of rotation is not coaxial with the second axis of rotation. In a more detailed embodiment, the stabilizing post is offset medially between about 0.1 millimeters to about 30 millimeters with respect to the first axis of rotation.

It is a twenty-sixth aspect to provide a prosthetic tibial insert comprising a prosthetic tibial tray insert including lateral and medial condyle receivers for receiving lateral and medial condyles of a femoral prosthesis, the medial condyle receiver has substantially greater conformity to the medial femoral condyle than does the lateral condyle receiver with respect to the lateral femoral condyle, the combination of lesser conformity laterally and substantially greater conformity medially creating rotation about a substantially vertical axis between the prosthetic tibial tray insert and the condyles of the femoral prosthesis, wherein the substantially greater conformity includes translational laxity between the medial condyle and the medical receiver of up to about 12.5 mm of translational laxity at greater than 20 degrees of knee flexion.

It is a twenty-seventh aspect to provide an implantable prosthetic knee joint comprising: (a) a femoral prosthetic; and (b) a tibial tray prosthetic including a prosthetic tibial tray insert rotationally repositionable with respect to the tibial tray about a first rotational axis, the tibial tray insert including medial and lateral spaced apart receivers for receiving a pair of condyles of the femoral prosthetic, the tibial tray insert also including a stabilizing post, where the first rotational axis is offset from a medial-lateral centerline of the tibial tray insert, and where the stabilizing post is offset from the medial-lateral centerline of the tibial tray insert.

In a more detailed embodiment of the twenty-seventh aspect, the femoral prosthetic includes a cam that is adapted to ride upon the stabilizing post of the tibial tray insert, and the cam is offset to correspond to the offset of the stabilizing post from the medial-lateral centerline of the tibial tray insert. In yet another more detailed embodiment, the cam is offset medially from the medial-lateral centerline of the tibial tray insert, and the cam is offset to the same extent as the offset of the stabilizing post from the medial-lateral centerline of the tibial tray insert. In a further detailed embodiment, the stabilizing post is offset medially between about 0.1 millimeters to about 30 millimeters from the medial-lateral centerline of the tibial tray insert, and the rotational axis is offset laterally between about 0.1 millimeters to about 30 millimeters from the stabilizing post. In still a further detailed embodiment, the rotational axis is offset laterally between about 0.1 millimeters to about 30 millimeters from the medial-lateral centerline of the tibial tray insert, and the stabilizing post is offset medially between about 0.1 millimeters to about 30 millimeters from the rotational axis.

It is a twenty-eighth aspect to provide an implantable prosthetic knee joint comprising: (a) a femoral prosthetic including a cam and a pair of condyles; and (b) a tibial tray prosthetic including a fixed bearing prosthetic tibial tray insert, the tibial tray insert including medial and lateral spaced apart receivers for receiving the pair of condyles of the femoral prosthetic, the tibial tray insert also including a stabilizing post, where the stabilizing post is offset from the medial-lateral centerline of the tibial tray insert, and where the cam is offset to correspond to the offset of the tibial tray insert.

In a more detailed embodiment of the twenty-eighth aspect, the stabilizing post is offset laterally from the medial-lateral centerline of the tibial tray insert, and the cam is offset to the same extent as the offset of the stabilizing post from the medial-lateral centerline of the tibial tray insert. In yet another more detailed embodiment, the stabilizing post is offset laterally between about 0.1 millimeters to about 30 millimeters from the medial-lateral centerline of the tibial tray insert, and the cam is offset laterally between about 0.1 millimeters to about 30 millimeters from the medial-lateral centerline of the tibial tray insert.

It is a twenty-ninth aspect to provide a prosthetic femoral component of a prosthetic knee joint comprising a prosthetic femoral component including a pair of spaced apart condyles and a cam interposing the condyles, the cam being offset from a medial-lateral centerline of the femoral component, where the cam is adapted to contact a stabilizing post of a tibial prosthetic assembly.

In a more detailed embodiment of the twenty-ninth aspect, the cam is offset laterally from the medial-lateral centerline of the femoral component. In yet another more detailed embodiment, the cam is offset medially from the medial-lateral centerline of the femoral component.

BRIEF DESCRIPTION OF THE DRAWINGS

FIG. 12($b$) and FIG. 12($c$) are pictorial representations of an exemplary MITKA PCR prosthetic having femoral radii for the lateral condyle being flatter, in contact with either a convex or sloped downward in the posterior direction tibial component.

FIGS. 14($c$) & ($d$) are pictorial profile representations of an exemplary MITKA posterior cruciate retaining TKA having an increased sloped between the lateral condyle and the tibial insert at varying degrees of knee flexion;

FIGS. 14($e$) & ($f$) are pictorial profile representations of an exemplary MITKA posterior cruciate retaining TKA with a lateral convex shape along which the lateral condyle rides at varying degrees of knee flexion;

DETAILED DESCRIPTION

Figure 1:
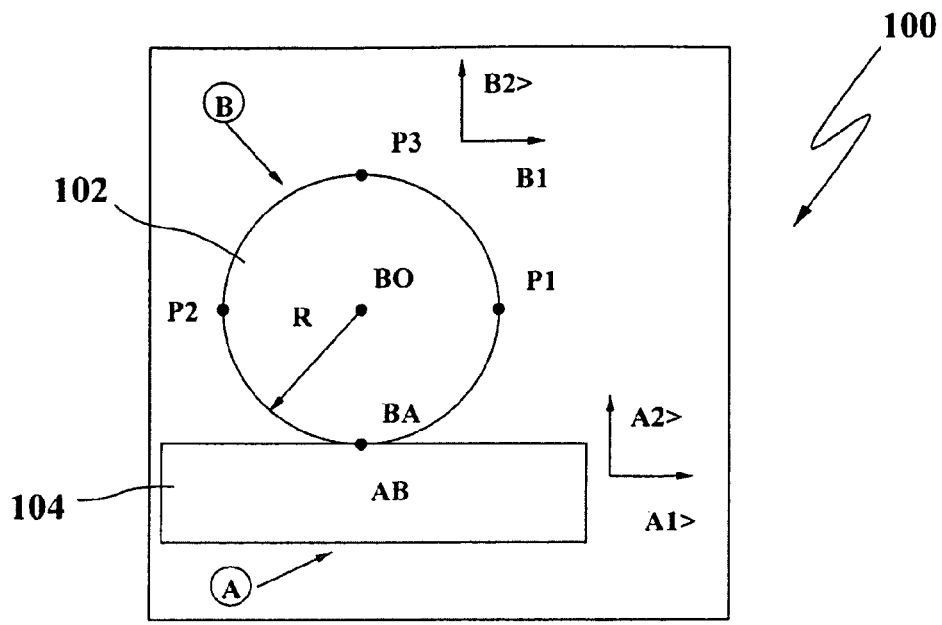
FIG. 1 is a free body diagram of a cylinder, B, contacting a platform, A.

The exemplary embodiments described and illustrated below encompass methods of inducing moments within an implanted prosthetic joint, as well as implantable prosthetic joints and components thereof inducing moments. Of course, it will be apparent to those of ordinary skill in the art that the embodiments discussed below are exemplary in nature and may be reconfigured without departing from the scope and spirit of the invention. However, for clarity and precision, the exemplary embodiments as discussed below may include optional steps, methods, and features that one of ordinary skill should recognize as not being a requisite to fall within the scope of the claims.

Basic principals governing the laws of mechanics are taken from Newton's Laws: (A) every object in a state of uniform motion tends to remain in that state of motion unless an external force is applied to it; (B) the relationship between an object's mass m, its acceleration a, and the applied force F, is F=ma; and, (C) for every action there is an equal and opposite reaction. The above laws of mechanics pertain to external forces applied to a system, however, when an in-plane force is applied to an object that has the ability to move, and if the applied force is greater than the resistive force (gravity, friction, etc.), the object will begin to move. Throughout knee flexion, whether during gait or into deep flexion, the cruciate ligaments of a natural knee force the tibia to internally rotate, levering the femur with respect to the tibia. It has been documented that the absence of the cruciate ligaments leads to a decrease in axial rotation.

For total knee arthroplasty (TKA) prosthetics, three primary forces may be exerted thereupon: (1) applied forces, which are produced by muscles passing across the knee joint; (2) bearing surface contact forces occurring between the femur and the tibia at the contact points and between the femur and the patella at the contact points; and, (3) constraint forces produced by ligaments resisting the active forces. However, the incidence and magnitude patterns of normal axial rotation of a knee prosthesis is governed by, and can only be induced to rotate by introducing moment arms with respect to active forces to cause rotation. In an exemplary system, a vector V has a distance D, with a line of action passing through a starting point P of the vector V. The moment M of the vector V about point P is characterized by Equation #1: M=R×V; where R is the position vector from point P to a second point along the vector V.

Before a moment analysis can be conducted for any TKA prosthetic, an understanding of the forces acting on the knee, both magnitude and direction, should be clearly determined and understood. The most effective method for deriving muscle, bearing surface and ligament forces, simultaneously, is through mathematical modeling techniques. It has been demonstrated that, with a proper understanding of knee mechanics, it is possible to derive equations to determine in vivo forces. Although it is important to know the magnitude of the forces applied at the knee, it is equally important to determine the direction of those applied forces. Proper direction of contact forces acting at the femorotibial and patellofemoral interfaces will ensure proper summation of the moments about a chosen point. Therefore, it is important to determine the direction of the velocity of the point on the femur, point FT, in contact with the tibia, which will allow for the determination of the direction of the bearing surface contact force occurring between points FT and TF, which is the point on the tibia in contact with the femur.

In a natural knee, like any mechanical system that has an) two objects in contact, three possible conditions could occur, which lead to vastly different conditions at the contact point between the two objects. These three conditions are: (1) pure rolling; (2) pure slipping; and, (3) a combination of rolling and slipping.

Referencing FIG. 1, an exemplary free-body diagram 100 includes a round cylinder (Body A) 102 with radius R moving with respect to a generally planar platform (Body B) 104 that is fixed in the Newtonian reference frame. In this simple example, two reference frames are defined for each object 102, 104, where the "A2>" and "B2>" directions are opposite of gravity. The point of contact between the objects 102, 104 is mutually defined by two points: point AB on the platform 104, and point BA on the cylinder 102. Three other points P1, P2, P3 are equidistantly spaced around the circumference of the cylinder 102, with the longitudinal center being identified by point BO. Point P1 is spaced a distance R in the A1> direction and a distance R in the A2> direction from point BA. Point P2 is spaced from point BA a distances R in the −A1> direction and R in the A2> direction. Point P3 is spaced a distance 2R in the A2> direction, from point BA.

Under pure rolling conditions, we can assume the velocity vector V_BO_A>=A1>, where: the radius R=1; and, the angular velocity of the cylinder ω, relative to the reference frame for the platform around the A3> axis, is equal to −A3>. One can then determine the velocity for points P1, P2, P3 and BO, which are determined using Equations #2-#5:

$$V\_P1\_A>=V\_BO\_A>+\omega\_B\_A>\times P\_BO\_P1>$$

$$V\_P1\_A>=A1>+-A3>\times A1>$$

$$V\_P1\_A>=A1>-A2> \quad \text{Equation \#2}$$

$$V\_BA\_A>=V\_BO\_A>+\omega\_B\_A>\times P\_BO\_BA>$$

$$V\_BA\_A>=A1>+-A3>\times -A2>$$

$$V\_BA\_A>=A1>-A1>=0> \quad \text{Equation \#3}$$

$$V\_P2\_A>=A1>+A2> \quad \text{Equation \#4}$$

$$V\_P3\_A>=2A1> \quad \text{Equation \#5}$$

Therefore, under pure rolling conditions, the velocity of point BA must equal the velocity of point AB. Since the platform 104 is "fixed" and not moving in the Newtonian reference frame, all points on the platform have a velocity equal to zero. This simple analysis shows that the velocity of point BA, on the cylinder 102, is equal to zero, under pure rolling conditions.

Under pure slipping conditions, the velocities for this same system, shown in FIG. 1, are different for each point along the cylinder 102. A practical way to describe pure slipping would be a car on ice. If the friction coefficient were equal to zero, the tires would spin, but the car would remain stationary. Therefore, in the knee, under pure slipping the V_BO_A>=0>, and similar to our example shown in FIG. 1, the Radius=1, ω=−A3>. Then the velocities for points BA, P1, P2, and P3 are determined using Equations #6-#9:

$$V\_P1\_A>=V\_BO\_A>+\omega\_B\_A>\times P\_BO\_P1>$$

$$V\_P1\_A>=0>+-A3>\times A1>$$

$$V\_P1\_A>=-A2> \quad \text{Equation \#6}$$

$V\_BA\_A{>}=V\_BO\_A{>}+\omega\_B\_A{>}{\times}P\_BO\_BA{>}$ $V\_BA\_A{>}=0{>}+{-}A3{>}{\times}{-}A2{>}$ $V\_BA\_A{>}={-}A1{>}$  Equation #7

$V\_P2\_A{>}=A2{>}$  Equation #8

$V\_P3\_A{>}=A1{>}$  Equation #9

Therefore, under pure slipping, the velocity of point BA is equal to $-A1{>}$, and the direction of the velocity is opposite in direction to posterior femoral rollback of the femoral condyles in a knee. Although it has been assumed that the velocity vector of the contact point between the femoral condyles and the tibial plateau would be in the posterior direction, under pure slipping, the correct direction of the velocity vector is in the anterior direction during flexion and in the posterior direction during extension. Although pure rolling and pure slipping have been described, it can be assumed that, under in vivo conditions, "only" pure rolling or "only" pure slipping conditions cannot occur.

Figure 2:
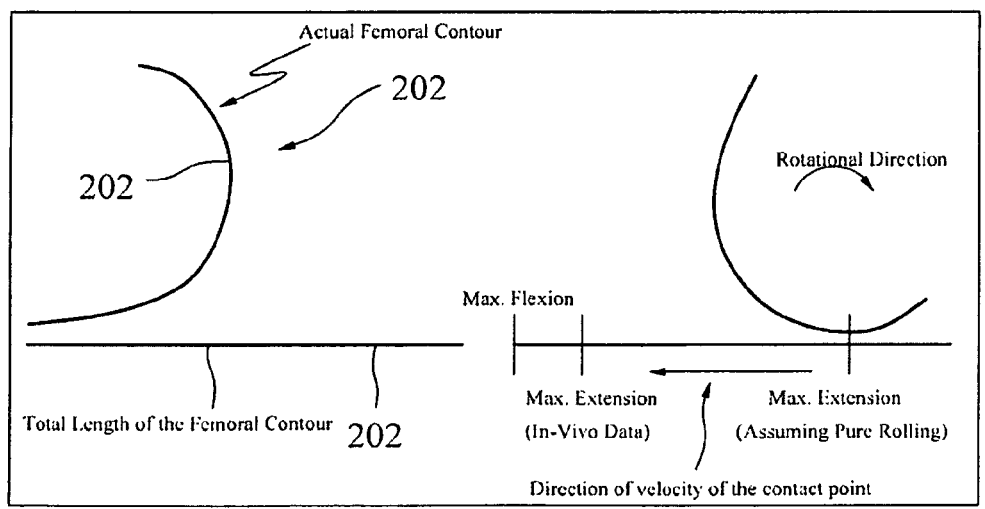
FIG. 2 is a diagram representing the curvature of a femoral condyle as a linear segment and showing the amount of the linear segment correspondingly contacted during flexion of the knee joint.

Referencing FIG. 2, a circumferential distance 200 of a prosthetic femoral condyle 202 can be represented by a flat line 204. Under pure rolling conditions, the prosthetic femoral condyle 202 would follow the flat line 204 path, which is much greater in distance than an anterior/posterior dimension of a prosthetic tibial insert (not shown). Previous analyses have documented that the amount of anterior posterior motion for a natural knee can range between 10 to 25 mm for the lateral condyle and, for a TKA prosthetic, this motion could be 10 mm in the anterior direction or 15 mm posterior. Thus, in a TKA prosthesis, the most dominant motion occurring at the contact point between the femoral condyle 202 and the tibial insert is slipping.

Referring again to FIG. 1, an analysis can be conducted to determine the velocities on the cylinder 102 at the bearing surface interface BA, AB when both slipping and rolling are present. In this analysis, we can assume $V\_BO\_A{>}=A1{>}$, radius $R=1$, and the angular velocity of the cylinder $\omega={-}2A3{>}$. Therefore, the velocities for points P1, P2, P3 and BA can be determined using Equations #10-#13:

$V\_P1\_A{>}=V\_BO\_A{>}+\omega\_B\_A{>}{\times}P\_BO\_P1{>}$ $V\_P1\_A{>}=A1{>}+{-}2A3{>}{\times}A1{>}$ $V\_P1\_A{>}=A1{>}{-}2A2{>}$  Equation #10

$V\_BA\_A{>}=V\_BO\_A{>}+\omega\_B\_A{>}{\times}P\_BO\_BA{>}$ $V\_BA\_A{>}=A1{>}+{-}2A3{>}{\times}{-}A2{>}$ $V\_BA\_A{>}=A1{>}{-}2A1{>}={-}A1{>}$  Equation #11

$V\_P2\_A{>}=A1{>}+2A2{>}$  Equation #12

$V\_P3\_A{>}=A1{>}{-}2A2{>}=3A2{>}$  Equation #13

Under all three conditions (slipping, rolling, or a combination), an important piece of information is the velocity of point BA. During pure rolling, the velocity of point BA is equal to zero, but under pure slipping and a combination of rolling and slipping, in our examples, this velocity is not equal to zero. Under pure slipping the direction of the velocity BA is in the $-A1{>}$ direction, opposite of the direction of posterior femoral rollback of the femoral condyles. During a combination of rolling and slipping, the direction of this velocity vector, $V\_BA\_N{>}$, in our example is in the $-A1{>}$, which is, again, in the opposite direction of contact point BA on AB. The magnitude of $V\_BA\_N{>}$ can change, depending on the velocity of BO and the angular velocity of body B in the Newtonian reference frame, but the magnitude will always be in the $-A1{>}$ direction. Therefore, it is disadvantageous to design a total knee arthroplasty prosthesis assuming that the forces at point BA on AB during knee flexion are in the $A1{>}$ (posterior direction) direction. Instead, one should design a total knee arthroplasty prosthesis with the forces being applied in the $-A1{>}$ direction (anterior direction) during knee flexion and in the $A1{>}$ direction during knee extension, similar to the direction of velocity vector acting at this point. Also, it should be noted, that during flexion the velocity of the contact point BA is equal to zero, under pure rolling and is in the anterior direction ($-A1{>}$) under pure slipping. Therefore, during knee flexion, $V\_BA\_N{>}$ is not in the posterior direction.

At present, all known TKA prosthetics are designed for equal distribution of forces at the contact points between the femoral components and the tibial components. Therefore, these TKA prosthetics do not incorporate moments to create axial rotation. During surgery, the goal of the surgeon is to create equal tension gaps between the femoral condyles and the tibial insert/plateau. If the amount of force acting between the medial condyle and the tibial insert is equal to the force acting between the lateral condyle and the tibial insert, it could be expected that the femoral components will not achieve axial rotation relative to the tibial insert because the medial and lateral condyle distances from the center of the tibial insert are also the same. If two forces act on a system and both forces are equal in magnitude and the moment arms to those forces, from a fixed point, are equal, then the moment of this system would be equal to zero.

Figure 3:
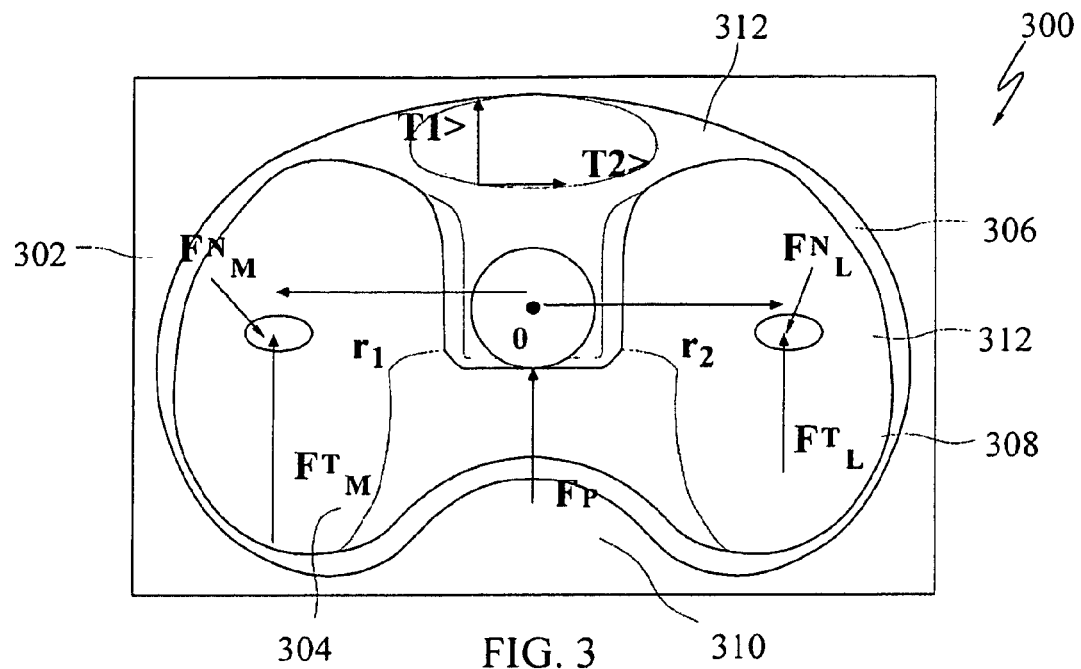
FIG. 3 is an overhead view of a prior art posterior stabilized mobile bearing total knee arthroplasty prosthetic insert having the polyethylene post aligned over the center of rotation.

Referencing FIG. 3, a typical posterior stabilized mobile bearing TKA prosthetic 300 accommodates five main contact forces: (1) the medial condyle force 302 in the vertical direction ($F^N_M$); (2) the medial condyle force 304 in the anterior/posterior direction ($F^T_M$); (3) the lateral condyle force 306 in the vertical direction ($F^N_L$); (4) the lateral condyle force 308 in the anterior/posterior direction ($F^T_L$); and (5) the force 310 applied by the cam on the post ($F_P$). Point O represents the rotation point of the polyethylene insert 312 relative to the tibial implant (not shown) about which moments are summated. Also included is the distance $r_1$ between point O to the medial condyle contact force, and the distance $r_2$ between point O to the lateral condyle.

If the moments are summated for the mobile bearing TKA prosthetic 300, around point O, in the $T3{>}$ direction (perpendicular to the $T1{>}$ and $T2{>}$ directions), the moment equation is represented by Equation #14:

$\Sigma M_O \cdot T3{>}=I \cdot \alpha \cdot T3{>}$  Equation #14

We can assume that the angular acceleration ($a$) of the polyethylene insert 312 relative to the tibial implant component in the $T3{>}$ direction is negligible, and can be set equal to zero. Therefore, with this presumption in place, Equation #14 can be refined into Equation #15:

$\Sigma M_O=0$ in the $T3{>}$ direction.

$\Sigma M_O \cdot T3{>}=-r_1 \cdot T2{>}{\times}F^T_M \cdot T1{>}+r_2 \cdot T2{>}{\times}F^T_L \cdot T1{>}$  Equation #15

Where the following information is known, the distance $r_1=r_2=r$, and the forces $F_M=F_L=F$, Equation #15 can be further simplified into Equation #16:

$\Sigma M_O \cdot T3{>}=-rF(-T3{>})+rF(-T3{>})$, $\Sigma M_O \cdot T3{>}=0$.  Equation #16

As shown by Equation #16, if the distances $r_1$, $r_2$ from the rotation point O of a mobile bearing TKA prosthetic 300 are the same to the medial and lateral condyles, the sum of the moments is equal to zero. Thus, the polyethylene insert 312 does not rotate about the tibial component. An in vivo analysis of the mobile bearing TKA prosthesis 300 evidenced that 7/9 subjects experienced less than 2.0 degrees of axial rotation.

Figure 4:
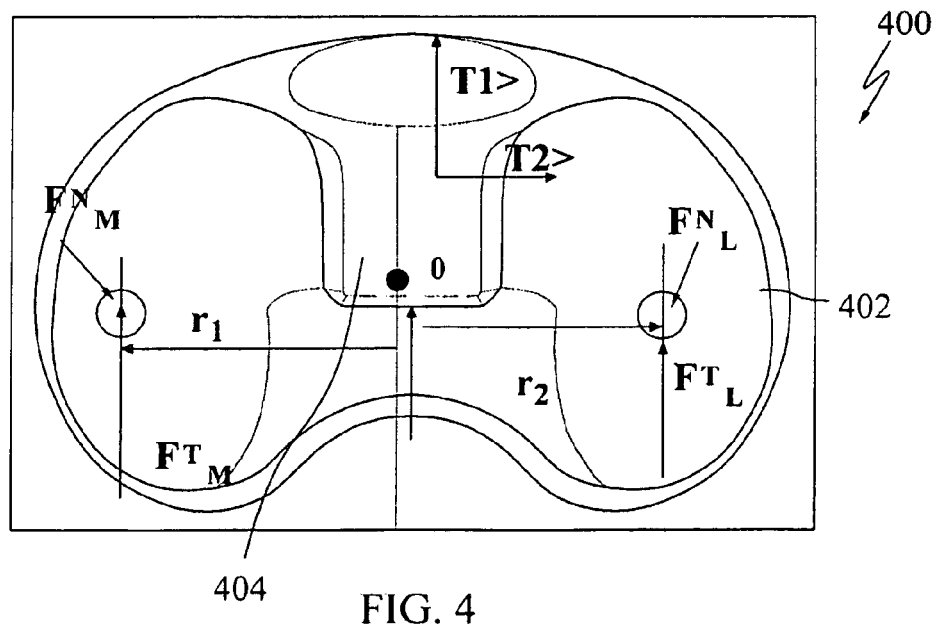
FIG. 4 is an overhead view of a prior art fixed bearing posterior stabilized total knee arthroplasty prosthetic insert having the polyethylene post located along the medial-lateral midline of the polyethylene insert.

Referring to FIG. 4, a typical fixed bearing TKA prosthetic 400 includes a tibial insert 402 (typically polyethylene) mounted to a tibial implant component (typically a metallic tibial tray, which is not shown). Unlike the mobile bearing posterior stabilized TKA prosthetic 300 of FIG. 3, the tibial insert 402 is fixed to the tibial implant component so that the insert does not rotate with respect to the tibial implant component. The forces acting on the fixed bearing posterior stabilized insert 402 are similar to those forces defined for the mobile bearing posterior stabilized TKA prosthetic 300 of FIG. 3.

Summation of moments acting on the fixed bearing polyethylene insert 402 can be conducted around the defined point O. The primary difference between the point O of FIG. 4, and point O of FIG. 3, is that the chosen point O does not represent a rotation point in FIG. 4, but rather a fixed physical point on the tibial insert 402 in the center of the post in the T2> direction. Summating the moments around point O is represented by Equation #14:

$$\Sigma M_O \cdot T3 \!\!>= I \cdot \alpha \cdot T3\!\!> \qquad \text{Equation \#14}$$

Similar to the mobile bearing TKA prosthetic 300 of FIG. 3, we can assume that the angular acceleration ($\alpha$) of the femur relative to the tibial insert 402 in the T3> direction is small, and can be set equal to zero. Therefore, with this presumption in place, Equation #14 can be refined into Equation #15:

$$\Sigma M_O = 0 \text{ in the } T3\!\!> \text{ direction.} \qquad \text{Equation \#15}$$

$$\Sigma M_O \cdot T3\!\!>= -r_1 \cdot T2\!\!> \times F^T_M \cdot T1\!\!> + r_2 \cdot T2\!\!> \times F^T_L \cdot T1\!\!>,$$

Where the following information is known, the distance $r_1 = r_2 = r$, and the forces $F_M = F_L = F$, Equation #15 can be further simplified into Equation #16:

$$\Sigma M_O \cdot T3\!\!>= -rF \cdot (-T3\!\!>) + rF \cdot (-T3\!\!>)$$

$$\Sigma M_O \cdot T3\!\!>= 0 \qquad \text{Equation \#16}$$

If the polyethylene post 404 is located in the center of the tibial insert 402, in the T1> and T2> directions, then the sum of the moments, in the T3> direction, for the contact forces applied by the femoral component on the tibial insert is equal to zero. Previous in vivo analyses of TKA prosthetics have determined that all TKA prosthetics achieve less axial rotation than a natural knee, while a significant number of TKA recipients are able to achieve less than two degrees of axial rotation of the resulting knee joint and approximately ⅓ of these recipients experience a reverse axial rotation pattern, opposite that of a natural knee.

Figure 5:
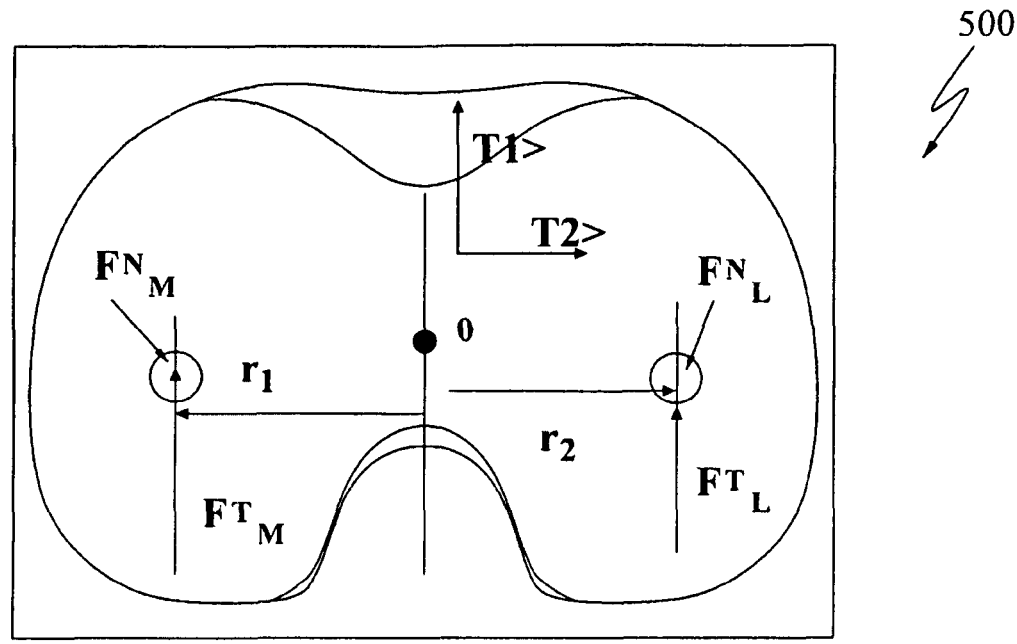
FIG. 5 is an overhead view of a prior art posterior cruciate retaining total knee arthroplasty prosthetic insert.

Referencing FIG. 5, a posterior cruciate retaining TKA prosthetic 500 (whether mobile or fixed bearing) allows for posterior cruciate ligament retention, without the presence of a cam/post mechanism 404 found in the posterior stabilized TKA prosthetic 400 of FIG. 4. The absence of the cam/post mechanism in a posterior cruciate retaining TKA prosthetic 500 leads to an analysis very similar to those for a posterior stabilized TKA prosthetics discussed above. Since the cam/post mechanism for present day posterior stabilized TKA prosthetics is in the center of the tibial insert, the cam/post force does not exert a moment. Therefore, when the cam/post mechanism does not induce rotation, the moment analysis for a mobile bearing posterior cruciate TKA prosthetic 500 will be similar to the moment analysis of a mobile bearing posterior stabilized TKA prosthetic 300 (see FIG. 3), and the moment analysis for a fixed bearing posterior cruciate retaining TKA prosthetic 500 will be similar to a fixed bearing posterior stabilized TKA prosthetic 400 (see FIG. 4), except for the resistive force of the posterior cruciate ligament. In other words, the sum of the moments for the contact forces applied by the femoral component on the tibial insert is equal to zero for these posterior cruciate retaining TKA prosthetics 500.

Figure 6:
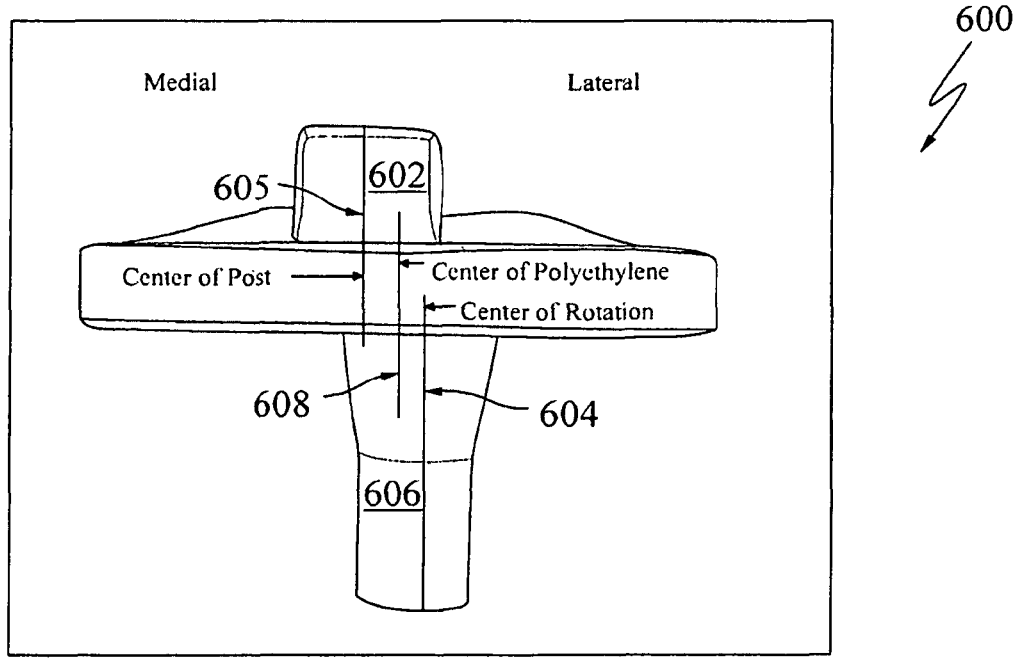
FIG. 6 is a rear, profile view of a first exemplary moment induced mobile bearing posterior stabilized total knee arthroplasty prosthetic in accordance with the present invention.

Referencing FIG. 6, an exemplary posterior stabilized mobile bearing Moment Induced Total Knee Arthroplasty (MITKA) prosthetic insert 600 is mounted to a prosthetic tibial stem 606, which is preferably implanted into a patient's tibia (not shown). The insert 600 includes a post 602 offset in the medial direction from the medial-lateral midline 608 of the insert 600 providing an axis of rotation 605 between the insert and a femoral component (not shown), and an axis of rotation 604 between the tibial stem 606 and the insert 600 that is shifted in the lateral direction from the medial-lateral midline 608.

Figure 7:
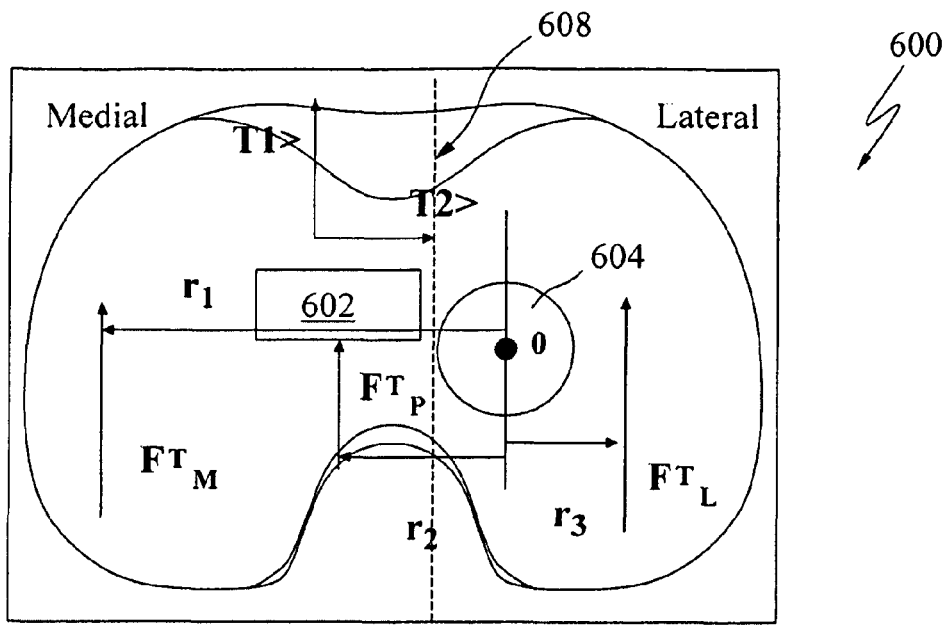
FIG. 7 is an overhead view of a first exemplary moment induced mobile bearing posterior stabilized total knee arthroplasty prosthetic insert in accordance with the present invention.

Referring to FIG. 7, a moment analysis of the exemplary MITKA prosthetic insert 600 includes summating the moments, around the point of rotation, O, in the T3> direction. The moment equation is represented by Equation #17:

$$\Sigma M_O \cdot T3\!\!>= -r_1 \cdot T2\!\!> \times F^T_M \cdot T1\!\!> - r_3 \cdot T2\!\!> \times F_P \cdot T1\!\!> + r_2 \cdot T2\!\!> \times F^T_L \cdot T1\!\!> \qquad \text{Equation \#17}$$

Where the following information is known, the distance $r_1 = 2r$, $r2 = r3 = r$, and the forces $F^T_M = F^T_L = F_P = F$, Equation #17 can be further simplified into Equation #18:

$$\Sigma M_O \cdot T3\!\!>= -2rF \cdot (-T3\!\!>) - rF \cdot (-T3\!\!>) + rF \cdot (-T3\!\!>)$$

$$\Sigma M_O \cdot T3\!\!>= 2rF \cdot T3\!\!> + rF \cdot T3\!\!> - rF \cdot T3\!\!>$$

$$\Sigma M_O \cdot T3\!\!>= 2rF \cdot T3\!\!> \qquad \text{Equation \#18}$$

In this exemplary moment summation, the moment induced by the exemplary MITKA prosthetic insert 600 is equal to 2rF, in the clockwise direction (looking down), leading to normal axial rotation of the tibial insert.

Unlike present day mobile bearing posterior stabilized TKA prosthetics 300 (see FIG. 3, for example), the tibial insert 600 for the MITKA knee will rotate in the clockwise direction (looking down) as a result of creating a distance between the rotation point O to the post 602 of the tibial insert 600 (distance represented by $r_3$), increasing the distance from the rotation point O to the medial condyle contact force $F^T_M$ (distance represented by $r_1$), and decreasing the distance from the rotation point O to the lateral condyle contact force $F^T_L$ (distance represented by $r_2$), allowing for the lateral condyle to move more posterior, similar to a natural knee.

Figure 8:
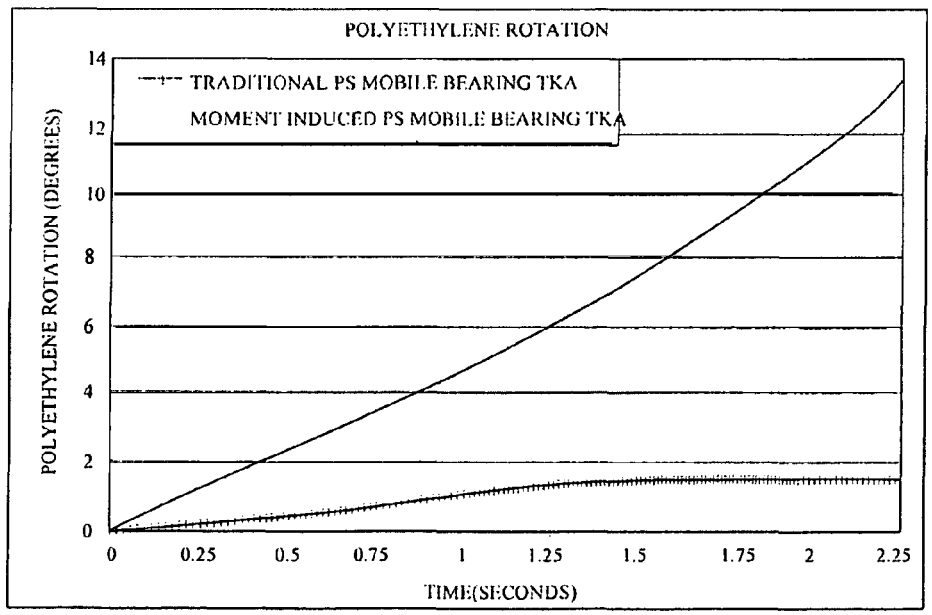
FIG. 8 is a plot of polyethylene rotation versus time for a prior art polyethylene tibial insert having the post and the rotation point in the center of the polyethylene, and the new moment induced posterior stabilized mobile bearing total knee arthroplasty prosthetic insert showing substantially greater rotation.

The amount of offset created between the post 602 and the rotation point O of the MITKA prosthetic insert 600 leads to increased axial rotation of the tibial insert relative to the tibial implant component (not shown) in the clockwise direction (T3> direction). An exemplary mathematical model has determined that a 3 mm shift of the post 602 in the medial direction from the centerline in the medial-lateral direction and a 3 mm shift of the rotation point O in the lateral direction from the centerline in the medial-lateral direction leads to 5 to 13 degrees of normal axial rotation, depending on the weight of the patient, the balancing of the knee, and the amount of force applied by the cam on the post (see FIG. 8). A second analysis was conducted using the exemplary mathematical model where the post 602 was shifted 6 mm in the medial direction and the rotation point O was shifted 6 mm in the lateral direction. The results for this analysis revealed the amount of normal axial rotation of the polyethylene increased to a range of 10 to 22 degrees of normal axial rotation, again, depending on the weight of the patient, the balancing of the knee, and the amount of force applied by the cam on the post. A third analysis, where the post 602 was shifted 10 mm in the medial direction and the rotation point O was shifted 10 mm in the lateral direction lead to normal axial rotation of the polyethylene ranging between 20 to 35 degrees, in the clockwise direction. Greater shifts in the medial and lateral direction are also within the scope of the disclosure, such as, without limitation, 0.01 to 20 millimeters of medial or lateral shift.

Figure 9:
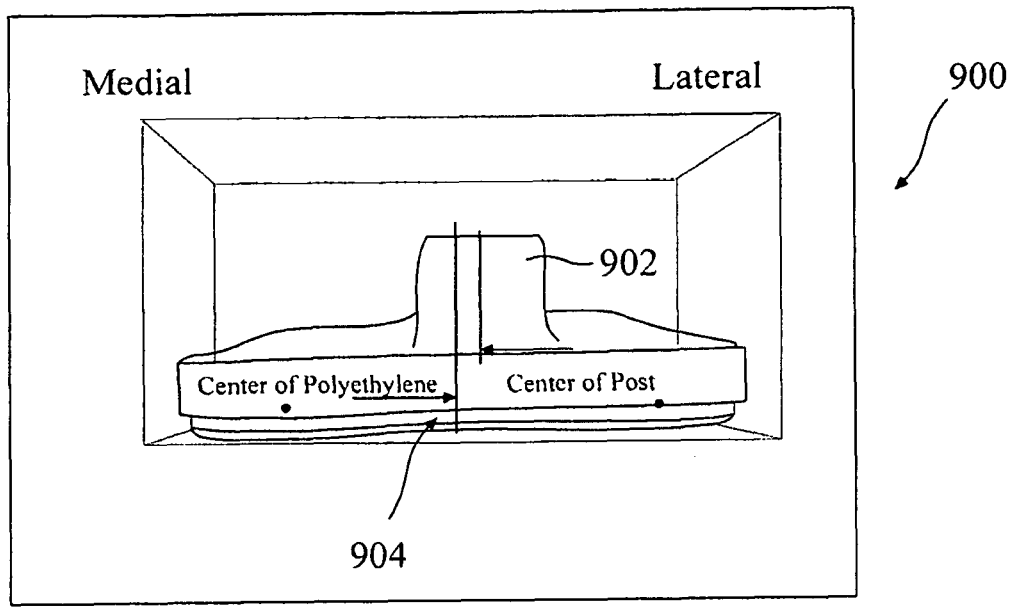
FIG. 9 is a rear profile view of a first exemplary moment induced fixed bearing posterior stabilized total knee arthroplasty prosthetic insert in accordance with the present invention.

Referencing FIG. 9, an exemplary posterior stabilized fixed bearing Moment Induced Total Knee Arthroplasty (MITKA) prosthetic insert 900 in accordance with an exemplary embodiment includes a cam/post mechanism 902 shifted in the lateral direction from the medial-later center 904 of the tibial insert. It is to be understood that the corresponding cam of the femoral component would be likewise shifted in the lateral direction to accommodate the shifted tibial post.

Figure 10:
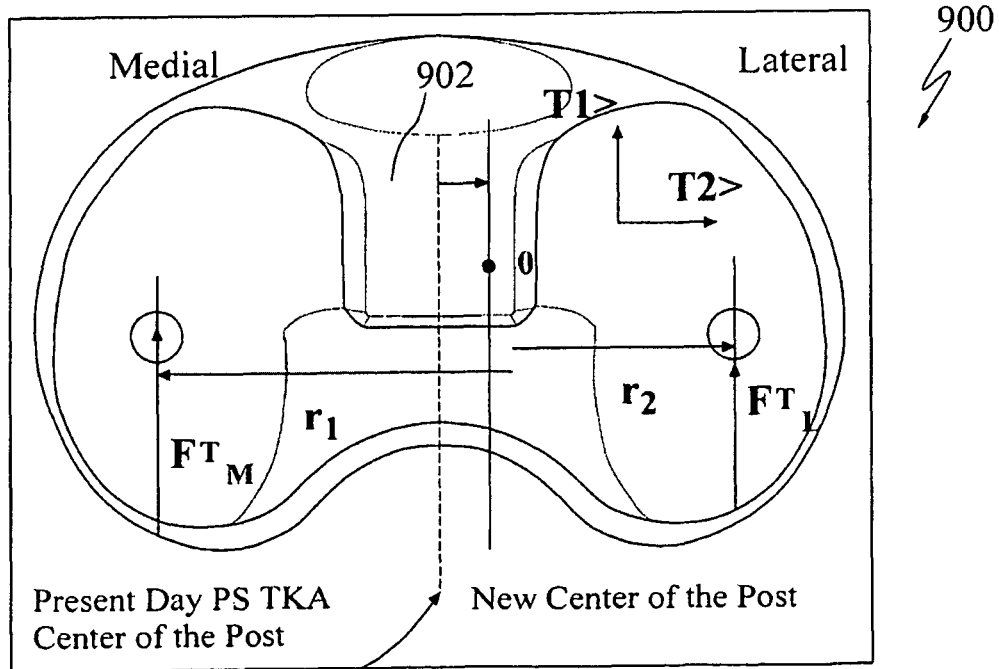
FIG. 10 is an overhead view of a first exemplary moment induced fixed bearing posterior stabilized total knee arthroplasty prosthetic insert in accordance with the present invention.

Referring to FIG. 10, a moment analysis of the exemplary fixed bearing PS MITKA prosthetic 900 insert includes summating the moments, around point of rotation O, in the T3> direction. The moment equation is represented by Equation #19:

$$\Sigma M_O \cdot T3 > = -r1 \cdot T2 > \times F^T_M \cdot T1 > + r2 \cdot T2 > \times F^T_L \cdot T1 > \qquad \text{Equation \#19}$$

Where the following information is known, the distance r1=2r, r2=r, and the forces $F^T_M = F^T_L = F$, Equation #19 can be further simplified into Equation #20:

$$\Sigma M_O \cdot T3 > = -2rF \cdot (-T3 >) + rF \cdot (-T3 >),$$

$$\Sigma M_O \cdot T3 > = 2rF \cdot T3 > -rF \cdot T3 >$$

$$\Sigma M_O \cdot T3 > = rF \cdot T3 > \qquad \text{Equation \#20}$$

In this exemplary moment summation, the moment induced by the exemplary MITKA prosthetic insert 900 is equal to rF, in the clockwise direction (looking down), leading to normal axial rotation of the femur relative to the tibial insert.

The amount of offset created between the post 902 and the rotation point O of the MITKA prosthetic insert 900 leads to increased axial rotation of the tibial insert relative to the tibial implant component (not shown) in the clockwise direction (T3> direction). An exemplary mathematical model has determined that a 3 mm shift of the post 902 in the lateral direction from the centerline in the medial-lateral direction leads to a femoral component rotation in the range of 2 to 8 degrees, depending on the weight of the patient, the balancing of the knee, and the amount of force applied by the cam on the post. If the post 902 is shifted 6 mm in the lateral direction, the amount of femoral component rotation increased to a range of 5 to 13 degrees, and if the post 902 was shifted 10 mm in the lateral direction, the amount of axial rotation again increased to a range of 9 to 25 degrees. Greater shifts in the medial and lateral direction are also within the scope of the disclosure, such as, without limitation, 0.01 to 20 millimeters of medial or lateral shift.

As discussed previously, the cam/post mechanism can be used in a posterior stabilized TKA prosthetic to generate rotation by creating a moment arm from the rotation point to the post of a mobile bearing TKA, or by shifting the post laterally, increasing the moment arm from the post to the medial condyle shear force. In the posterior cruciate retaining TKA, moments are primarily induced by offsetting the rotation point and building up conformity between the femoral radii and the concave tibial insert radii.

Figure 11:
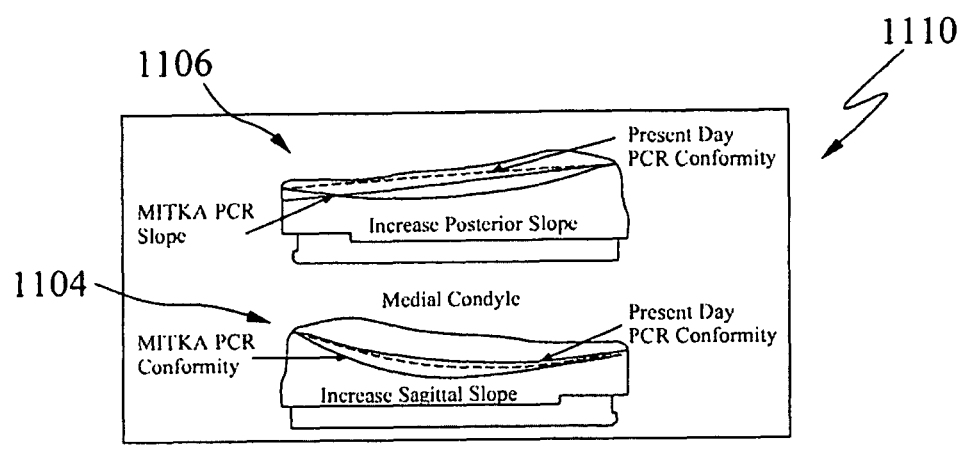
FIG. 11 are medial and lateral profile views of exemplary changes in medial condyle conformity and increased lateral condyle posterior slope for the exemplary prosthetic inserts of the present invention.

Referencing to FIG. 11, an exemplary MITKA posterior cruciate retaining (PCR) fixed bearing prosthetic insert 1100 in accordance with the present disclosure includes a medial receiver 1104 and a lateral receiver 1106 that are adapted to receive the medial and lateral condyles, respectively, of a femoral prosthesis (not shown). In order to rotate the tibial insert 1100 clockwise (looking down), the insert 1100 includes greater conformity between the medial condyle and the medial receiver 1104 on the medial side of the tibial insert. In this exemplary embodiment 1100, the radii of the medial receiver 1104 is greater than the radii of the medial condyle, allowing for anterior/posterior translation to occur between the medial condyle and the medial receiver. Increased conformity between the medial receiver 1104 and the medial condyle leads to an increased shear force applied by the medial condyle on the medial receiver of the polyethylene insert, causing a clockwise moment to occur, especially if the superior surface of lateral side of the tibial insert 1100 is either flat or convex in shape, coupled with a flatter shape for the lateral condyle of the femoral prosthesis.

Figures 12A, 12B, 12C:
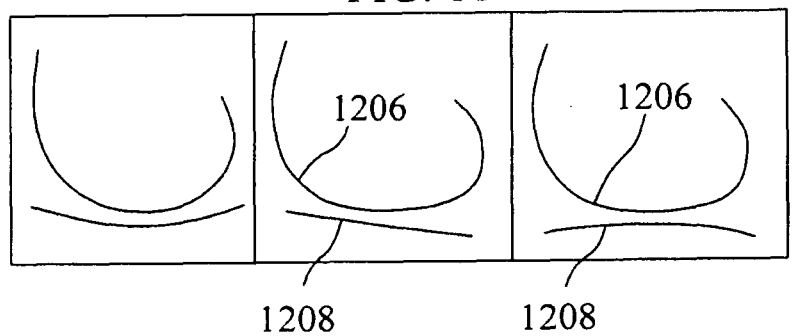
FIG. 12($a$) is a pictorial representation of a prior art lateral femoral condyle PCR TKA prosthetic having a rounded convex shape.
Figure 13:
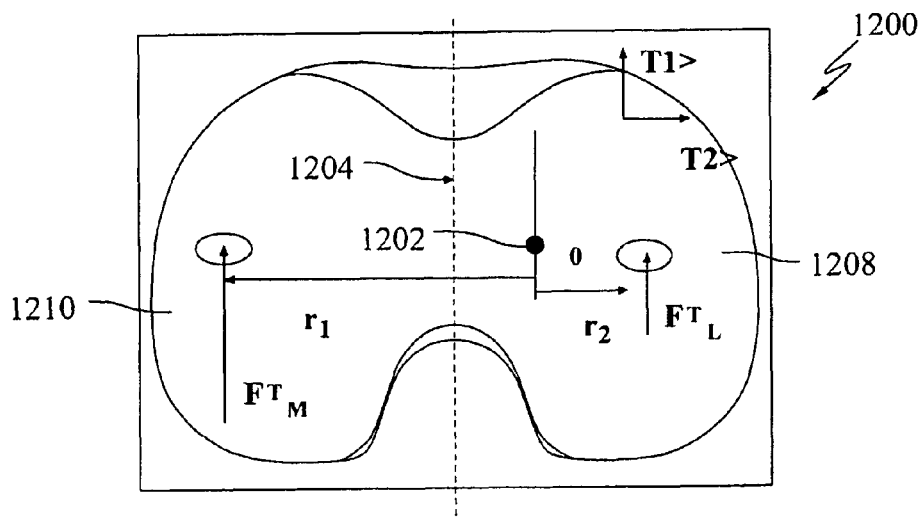
FIG. 13 is an overhead view of a first exemplary moment induced mobile bearing posterior stabilized total knee arthroplasty prosthetic insert in accordance with the present invention.

Referencing FIGS. 12 and 13, an exemplary MITKA mobile bearing PCR prosthetic insert 1200 includes the rotation point 1202 (and rotational axis) moved in the lateral direction with respect to the center 1204 of the tibial implant baseplate (not shown) using the contours between the insert 1200 and the femoral condyles 1206, 1208. On the lateral side, the lateral femoral condyle 1206 is flatter (similar to the shape of a canoe) and the lateral receiver 1208 of the tibial insert is either sloped downward in the anterior-to-posterior direction (see FIG. 12(*b*)) or convex (see FIG. 12(*c*)). On the medial side, the medial femoral condyle includes greater conformity with the medial receiver 1210 on the medial side of the tibial insert 1200. Therefore, as the shear force between the femoral condyles and the tibial insert increases, the amount of shear force will be greater on the medial side and induce a clockwise rotation of the tibial insert due to: (1) the increased conformity; and (2) the moment arm from the rotation point to the medial shear force being greater than the moment arm from the rotation point to the lateral condyle force.

One of the main goals for achieving increased weight-bearing flexion for a total knee arthroplasty is the ability to move the lateral condyle in the posterior direction. In the normal knee, this can be achieved through axial rotation or translation of both condyles. Since, in the normal knee, the medial condyle does not move more than 10 mm in the posterior direction and on average, this amount is less than 5 mm, the lateral condyle achieves posterior contact through femorotibial axial rotation. Moments are introduced in the MITKA so that normal axial rotation could occur and the lateral condyle can achieve greater posterior contact with increasing knee flexion. This inducement of moments is more easily accomplished with a posterior stabilized TKA, where the cam/post force could be used to drive rotation in the clockwise direction or to lever the medial condyle force with respect to the post. In the posterior cruciate ligament retaining TKA, the ability to induce moments is more involved. The MITKA posterior cruciate ligament retaining knee uses increased conformity between the medial condyle and the medial receiver of the polyethylene insert. Also, an increased radius of curvature for the lateral condyle (canoe shaped) allows the lateral condyle contact point to move in the posterior direction within the first 30 degrees of knee flexion. Therefore, the goal of achieve posterior contact with the lateral condyle, with increasing knee flexion can be accomplished in MITKA posterior cruciate ligament retaining TKA through the introduction of moments and by changing the geometrical shapes of the femoral condyles. In this manner, the axis of rotation between the MITKA mobile bearing PCR prosthetic insert 1200 and the femoral prosthetic can be shifted from the medial-lateral centerline of the insert 1200 (and also from the anterior-posterior centerline), while the axis of rotation between the MITKA mobile bearing PCR prosthetic insert 1200 and the tibial prosthetic tray (not shown) can be shifted from the medial-lateral centerline of the insert 1200 (and also from the anterior-posterior centerline of the insert 1200).

Although the increased conformity between the medial condyle and the receiver in medial aspect of the tibial polyethylene insert and the flatter lateral condyle, contacting either a posterior sloped or convex shaped lateral aspect of the polyethylene insert has been previously described herein for a posterior cruciate retaining TKA, these design features can be used in any TKA prosthetic type. The above mentioned design changes could be used in a PS TKA type to increase axial rotation and could be used in an anterior and posterior cruciate retaining TKA type to ensure normal axial rotation.

In the exemplary prosthetic inserts of the present disclosure, the amount of medial condyle conformity with respect to the medial receiver of the tibial insert may play a significant role. An additional factor that may play a significant role in axial rotation, leading to an increase or decrease in the amount of axial rotation described herein, is condylar balancing at the time of surgery. It is to be understood that the mathematical models referenced in the aforementioned discussion incorporated medial and lateral condyle flexion gaps, during intra-operative ligament balancing, that were equal, leading to the medial condyle contact force being equal to the lateral condyle contact force. If the medial condyle contact force is greater than the lateral condyle contact force, the amount of normal axial rotation would increase over those values predicted by the above-referenced mathematical model. In contrast, if the lateral condyle contact force is greater than the medial condyle contact force, the amount of axial rotation would fall below those values predicted by the model.

Figure 14:
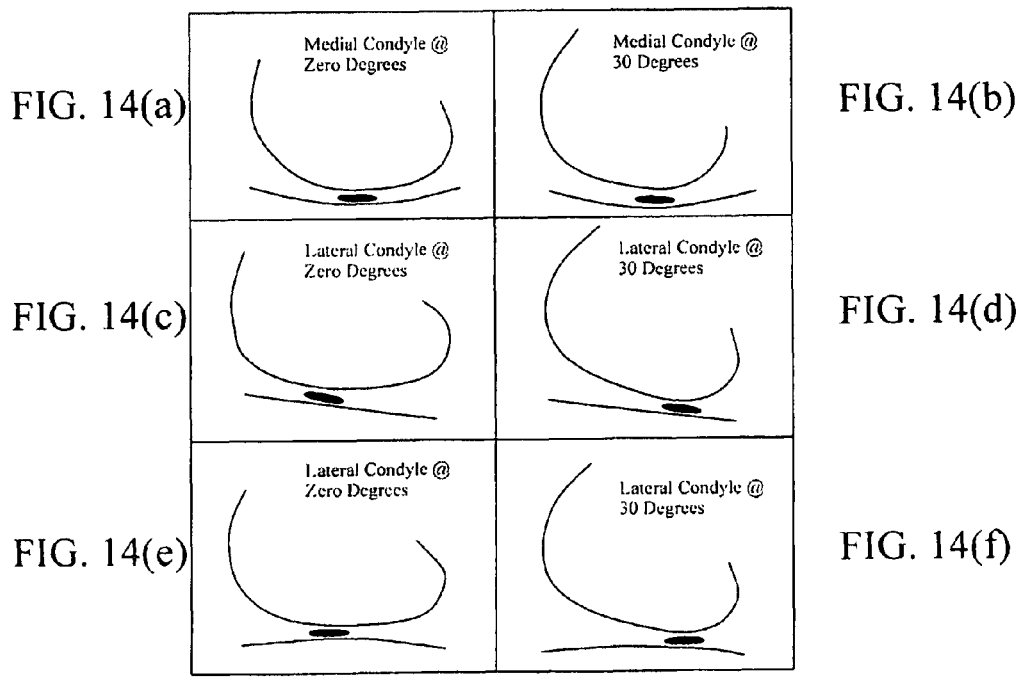
FIGS. 14($a$) & ($b$) are pictorial profile representations of an exemplary MITKA posterior cruciate retaining TKA having increased conformity between the medial condyle and the medial receiver of the tibial insert at varying degrees of knee flexion.

Referencing FIG. 14, the exemplary MITKA posterior cruciate retaining TKA prosthetic includes increased conformity between the medial condyle and the medial receiver of the tibial (polyethylene) insert in order to induce a clockwise moment of the femur relative to the tibia (normal axial rotation) (see FIGS. 14(*a*) & (*b*)). Also, the lateral condyle will achieve greater posterior motion due to the flatter condylar geometry (canoe shaped) at full extension leading a rapid change of the contact position from full extension to 30 degrees of knee flexion. This posterior change of the contact position for the lateral condyle may be further assisted by the increased posterior slope of the polyethylene insert (see FIGS. 14(*c*) & (*d*)) or the convex shape of the polyethylene insert (see FIGS. 14(*e*) & (*f*)).

Figure 15:
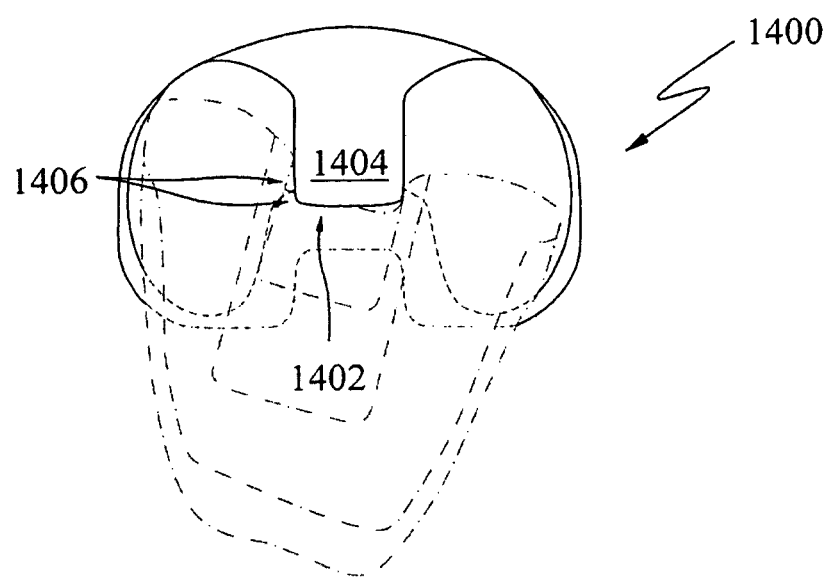
FIG. 15 is a 3-D overhead, perspective view of a prior art MITKA prosthetic cam/post mechanism with flat leading surfaces.

Referring to FIG. 15, all cam/post mechanisms in present-day TKA prosthetics 1400 include flat surfaces. These flat surfaces lead to the hypothesis that the contact areas would be large, thereby leading to less stress applied by the cam 1402 onto the post 1404. Unfortunately, if rotation of the femoral component (the cam) 1402 occurs with respect to the tibial insert (the post) 1404 in a fixed bearing posterior stabilized TKA prosthetic, the opposite is true and the contact area 1406 between the femoral cam and the tibial post becomes very small. A primary concern for decreased contact areas between the flat cam 1402 on a flat post 1404 is edge loading, leading to high stresses that lead to premature tibial insert failure at the post.

Figure 16:
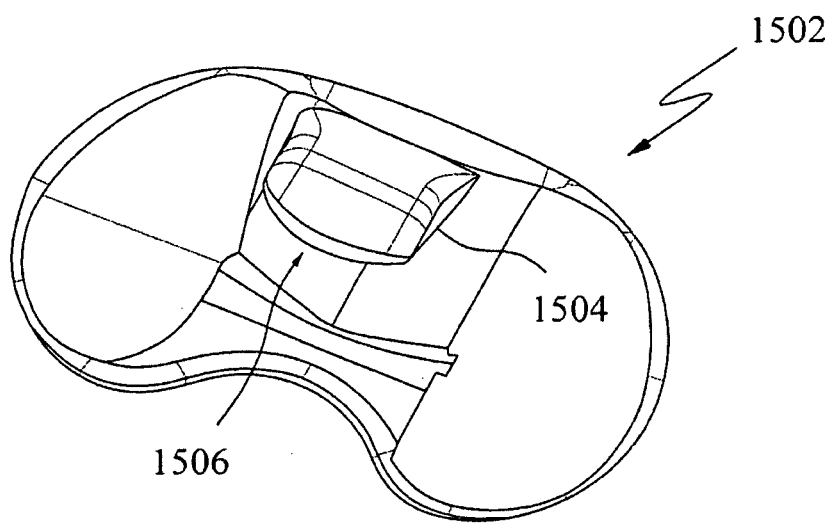
FIG. 16 is an elevated perspective view of an exemplary MITKA posterior stabilized prosthetic insert.
Figure 17:
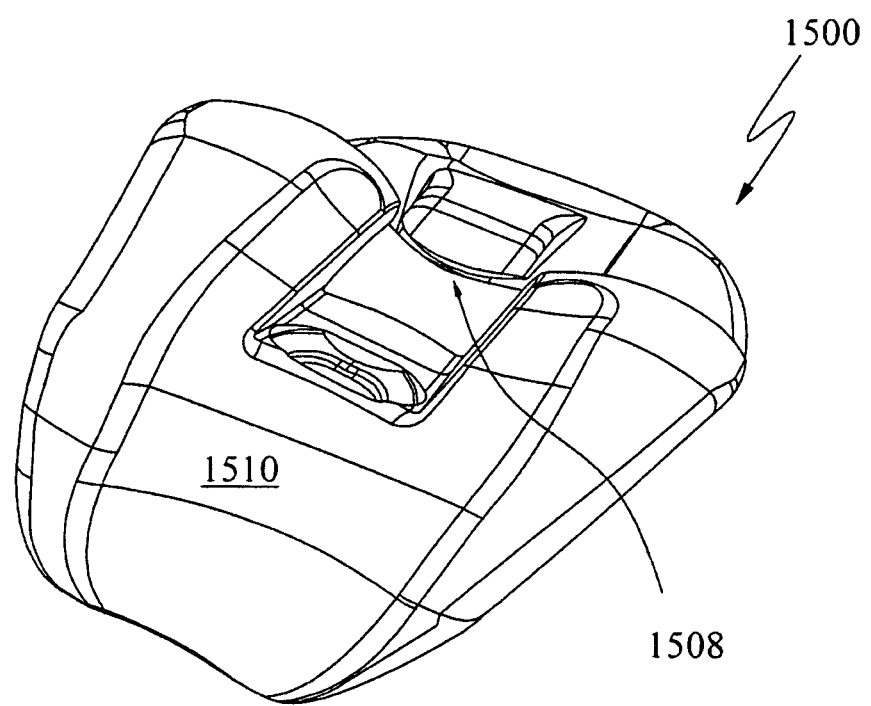
FIG. 17 is an elevated perspective view of an exemplary MITKA posterior stabilized prosthetic device.

Referencing FIGS. 16 and 17, an exemplary MITKA posterior stabilized TKA prosthetic device 1500 in accordance with the present disclosure includes a tibial insert 1502 with a tibial post 1504 having a rounded posterior surface 1506. This rounded posterior surface 1506 of the post 1502 is adapted to interact with a rounded femoral cam 1508 of a femoral prosthetic component 1510. The radius R for the rounded posterior surface 1506 of the post 1504 and the rounded cam 1508 are the similar, but the chosen value of R for the MITKA fixed bearing posterior stabilized prosthetic device 1500 will depend on the amount of rotation desired. If the MITKA posterior stabilized prosthetic device 1500 is designed to incorporate minimal femorotibial axial rotation, then the value for R will be higher than the value for R if the MITKA posterior stabilized prosthetic device 1500 is designed for greater axial rotation.

While the aforementioned exemplary MITKA posterior stabilized prosthetics have been explained using a tibial component with an integral post that is adapted to interface with a cam of the femoral prosthetic component, it is also within the scope of the disclosure to incorporate the post into the femoral component and the cam into the tibial insert. Likewise, while the aforementioned exemplary prosthetics have been explained using a tibial component with an integral post adapted to interface with a cavity within the tibial insert, it is also within the scope of the disclosure to incorporate the post into the tibial insert, where the post would be correspondingly received by a cavity within the tibial implant.

While the aforementioned exemplary MITKA mobile bearing POR prosthetics have been explained by shifting the post and point of rotation between the insert and tibial component, it should be understood that one might only shift the post or only shift the point of rotation to create the moments discussed herein. An exemplary embodiment would include a POR prosthetic device having a post aligned along the medial-lateral midline, while the point of rotation between the insert and tibial component (tray) would be offset from the medial-lateral midline. Conversely, an exemplary POR prosthetic device may have its point of rotation aligned along the medial-lateral midline, while the post would be offset from the medial-lateral midline.

It is also within the scope of the disclosure to shift of the contact point of the post or point of rotation anteriorly or posteriorly. Mobile bearing prior art prosthetic knee inserts have always had the point of rotation centered along the medial-lateral midline and along the anterior-posterior midline. By shifting the contact point of the post or point of rotation from the prior art centered position, moments are introduced if the point of contact of the post and point of rotation are not coaxial.

Those skilled in the art will readily understand that the exemplary inserts of the instant disclosure are adapted for use in prosthetic knee joints comprising tibial and femoral components. The plethora of tibial implants and femoral implants that the exemplary embodiments of the instant disclosure may be incorporated with, or used in place of, defies an exhaustive listing.

Following from the above description and exemplary embodiments, it should be apparent to those of ordinary skill in the art that, while the methods and apparatuses herein described constitute exemplary embodiments, the invention is not limited to these precise embodiments and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

I claim:

1. A prosthetic knee implant system comprising:
   a distal femoral implant component having a medial condyle, a lateral condyle and a cam between the condyles;
   a tibial tray;
   a mobile bearing tibial tray insert including a medial condyle receiver spaced apart from a lateral condyle receiver;
   the tibial tray and mobile bearing tibial tray insert including a complementary recess and projection sized and shaped for rotational mounting of the mobile bearing tibial tray insert on the tibial tray;
   the mobile bearing tibial tray insert also including a stabilizing post positioned to engage the cam of the distal femoral implant component during articulation; and
   wherein the mobile bearing tibial tray insert has a medial-lateral centerline, the stabilizing post has a medial-lateral centerline offset medially from the medial-lateral centerline of the mobile bearing tibial tray insert, and the complementary recess and projection define a substantially vertical rotational axis offset laterally from the medial-lateral centerline of the stabilizing post.

2. The prosthetic knee implant system of claim 1, wherein the substantially vertical rotational axis is offset laterally about 0.1 to about 30 mm from the medial-lateral centerline of the mobile bearing tibial tray insert.

3. The prosthetic knee implant system of claim 1, wherein the stabilizing post is offset medially about 0.1 to about 30 mm from the medial-lateral centerline of the mobile bearing tibial tray insert.

4. The prosthetic knee implant system of claim 3, wherein the substantially vertical rotational axis is offset laterally about 0.1 to about 30 mm from the medial-lateral centerline of the mobile bearing tibial tray insert.

5. The prosthetic knee implant system of claim 1, wherein:
   the medial condyle receiver and the medial condyle are shaped so that there is relative translational laxity between the medial condyle and the medial condyle receiver during flexion of the knee.

6. The prosthetic knee implant system of claim 5, wherein the medial condyle receiver and the medial condyle are shaped to have up to 12.5 mm of translational laxity at greater than 20 degrees of knee flexion.

7. A prosthetic knee implant system comprising:
   a distal femoral implant component having a medial condyle and a lateral condyle; a tibial tray; a mobile bearing tibial tray insert rotatably mountable on the tibial tray for articulation with the distal femoral implant component, the mobile bearing tibial tray insert including a medial condyle receiver spaced apart from a lateral condyle receiver, the mobile bearing tibial tray insert also including a stabilizing post positioned to engage a portion of the distal femoral implant component during articulation, the stabilizing post having a medial-lateral centerline, where the mobile bearing tibial tray insert rotates with respect to the tibial tray around a substantially vertical first rotational axis offset laterally from the medial-lateral centerline of the stabilizing post and the distal femoral implant component rotates with respect to the tibial tray insert about a substantially vertical second rotational axis offset medially from the first rotational axis.

8. The prosthetic knee implant system of claim 7, wherein the first rotational axis is offset laterally from a medial-lateral centerline of the mobile bearing tibial tray insert.

9. The prosthetic knee implant system of claim 7, wherein the first rotational axis is offset anteriorly from an anterior-posterior centerline of the mobile bearing tibial tray insert.

10. The prosthetic knee implant system of claim 7, wherein the first rotational axis is offset posteriorly from an anterior-posterior centerline of the mobile bearing tibial tray insert.

11. The prosthetic knee implant system of claim 7, wherein the stabilizing post is offset between about 0.1 millimeters to about 30 millimeters medially from a medial-lateral centerline of the mobile bearing tibial tray insert.

12. The prosthetic knee implant system of claim 7, wherein the stabilizing post is offset medially between about 0.1 millimeters to about 30 millimeters with respect to the first rotational axis.

13. The prosthetic knee implant system of claim 7, wherein:
   the lateral condyle receiver includes at least one of a convex shape or a sequentially sloped from anterior to posterior shape; and
   the medial condyle receiver includes a concave shape.

14. The prosthetic knee implant system of claim 7, wherein a posterior aspect of the stabilizing post is not rounded.

15. The prosthetic knee implant system of claim 7, wherein the stabilizing post is offset anteriorly from an anterior-posterior centerline of the mobile bearing tibial tray insert.

16. The prosthetic knee implant system of claim 7, wherein the stabilizing post is offset posteriorly from an anterior-posterior centerline of the mobile bearing tibial tray insert.

17. The prosthetic knee implant system of claim 7, wherein the mobile bearing tibial tray insert includes a recess adapted to receive a projection from the tibial tray allowing the mobile bearing tibial tray insert to rotate with respect to the tibial tray about the first rotational axis.

18. The prosthetic knee implant system of claim 7, wherein the mobile bearing tibial tray insert includes a projection adapted to be received by a recess within the tibial tray allowing the mobile bearing tibial tray insert to rotate with respect to the tibial tray about the first rotational axis.

19. The prosthetic knee implant system of claim 7, wherein
   there is translational laxity between the medial condyle receiver and the medial condyle during flexion of the knee.

20. The prosthetic knee implant system of claim 7, wherein the medial condyle receiver and the medial condyle are shaped
   to have up to 12.5 mm of translational laxity at greater than 20 degrees of knee flexion.

21. The prosthetic knee implant system of claim 7, wherein a posterior aspect of the stabilizing post is rounded.

22. The prosthetic knee implant knee system of claim 7, wherein the medial condyle is larger than the lateral condyle.

* * * * *